United States Patent
Bergmann

(10) Patent No.: US 10,598,674 B2
(45) Date of Patent: Mar. 24, 2020

(54) ADRENOMEDULLIN TO GUIDE THERAPY OF BLOOD PRESSURE DECLINE

(71) Applicant: SphingoTec GmbH, Hennigsdorf (DE)

(72) Inventor: Andreas Bergmann, Berlin (DE)

(73) Assignee: SphingoTec GmbH, Hennigsdorf (DE)

( * ) Notice: Subject to any disclaimer, the term of this patent is extended or adjusted under 35 U.S.C. 154(b) by 0 days.

(21) Appl. No.: 14/778,114

(22) PCT Filed: Mar. 19, 2014

(86) PCT No.: PCT/EP2014/055554
§ 371 (c)(1),
(2) Date: Sep. 18, 2015

(87) PCT Pub. No.: WO2014/147153
PCT Pub. Date: Sep. 25, 2014

(65) Prior Publication Data
US 2017/0010286 A1    Jan. 12, 2017

(30) Foreign Application Priority Data
Mar. 20, 2013    (EP) .................................. 13160265

(51) Int. Cl.
*A61K 39/395* (2006.01)
*C07K 16/26* (2006.01)
*G01N 33/68* (2006.01)
*G01N 33/74* (2006.01)

(52) U.S. Cl.
CPC ............ *G01N 33/74* (2013.01); *C07K 16/26* (2013.01); *G01N 33/6893* (2013.01); *G01N 2333/575* (2013.01); *G01N 2800/26* (2013.01)

(58) Field of Classification Search
None
See application file for complete search history.

(56) References Cited

U.S. PATENT DOCUMENTS

| | | |
|---|---|---|
| 5,639,855 A | 6/1997 | Kitamura et al. |
| 5,830,703 A | 11/1998 | Kitamura et al. |
| 5,837,823 A | 11/1998 | Kitamura et al. |
| 5,910,416 A | 6/1999 | Kitamura et al. |
| 2007/0212742 A1* | 9/2007 | Bergmann ........... G01N 33/574 435/7.93 |
| 2009/0191220 A1* | 7/2009 | Bergmann ............. C07K 16/22 424/172.1 |
| 2009/0304673 A1* | 12/2009 | Buchberger ....... A61K 38/4886 424/94.67 |
| 2010/0035289 A1* | 2/2010 | Bergmann ......... G01N 33/6893 435/15 |
| 2013/0177901 A1* | 7/2013 | Darbouret ............ G01N 33/689 435/6.1 |

FOREIGN PATENT DOCUMENTS

EP    0622458 A2    11/1994

OTHER PUBLICATIONS

Bangash et al. (012. Brit. J. Pharma. 165:2015-2033.*
Gouya et al. 2011. PLoS One 6:e17803.*
Correa et al. 2013 17:R21, published Jan. 30, 2013.*
Singer et al. 2016. JAMA 315:801-810 (Year: 2016).*
International Search Report dated Apr. 22, 2014 issued in corresponding PCT/EP2014/055554 application (pp. 1-5).
A.S. Belloni et al., "Proadrenomedullin-Derived Peptides as Autocrine-Paracrine Regulators of Cell Growth", Histology and Histopathology, vol. 16 (2001) pp. 1263-1274.
M. Mahata et al., "Proadrenomedullin N-Terminal 20 Peptide: Minimal Active Region to Regulate Nicotinic Receptors", Hypertension, vol. 32, No. 5 (Nov. 1, 1998) pp. 907-916.
M.R. Nandalur et al., "Vasopressor Use in the Critical Care Unit for Treatment of Persistent Post-carotid Artery Stent Induced Hypotension", Neurocritical Care, vol. 7, No. 3 (Aug. 1, 2007) pp. 232-237.
M.M. Taylor et al., "Ribozyme Compromise of Adrenomedullin mRNA Reveals a Physiological Role in the Regulation of Water Intake", Am J Physiol Regulatory Integrative Comp Physiol, vol. 282 (2002) pp. R1739-R1745.

* cited by examiner

*Primary Examiner* — Shulamith H Shafer
(74) *Attorney, Agent, or Firm* — Millen, White, Zelano & Branigan, PC; Ryan Pool

(57) ABSTRACT

Subject matter of the present invention is an in vitro method for identifying a subject in need of administration of fluid resuscitation or a vasopressor comprising the following steps:
Determining the level of proADM and/or fragments thereof having at least 6 amino acids in a bodily fluid of said subject
Correlating said level with the need of said patient for fluid resuscitation or administration of a vasopressor wherein said patient is identified as having such a need if the level of proADM and/or fragments thereof having at least 6 amino acids in the bodily fluid of said subject is above a threshold.

Figure 1:
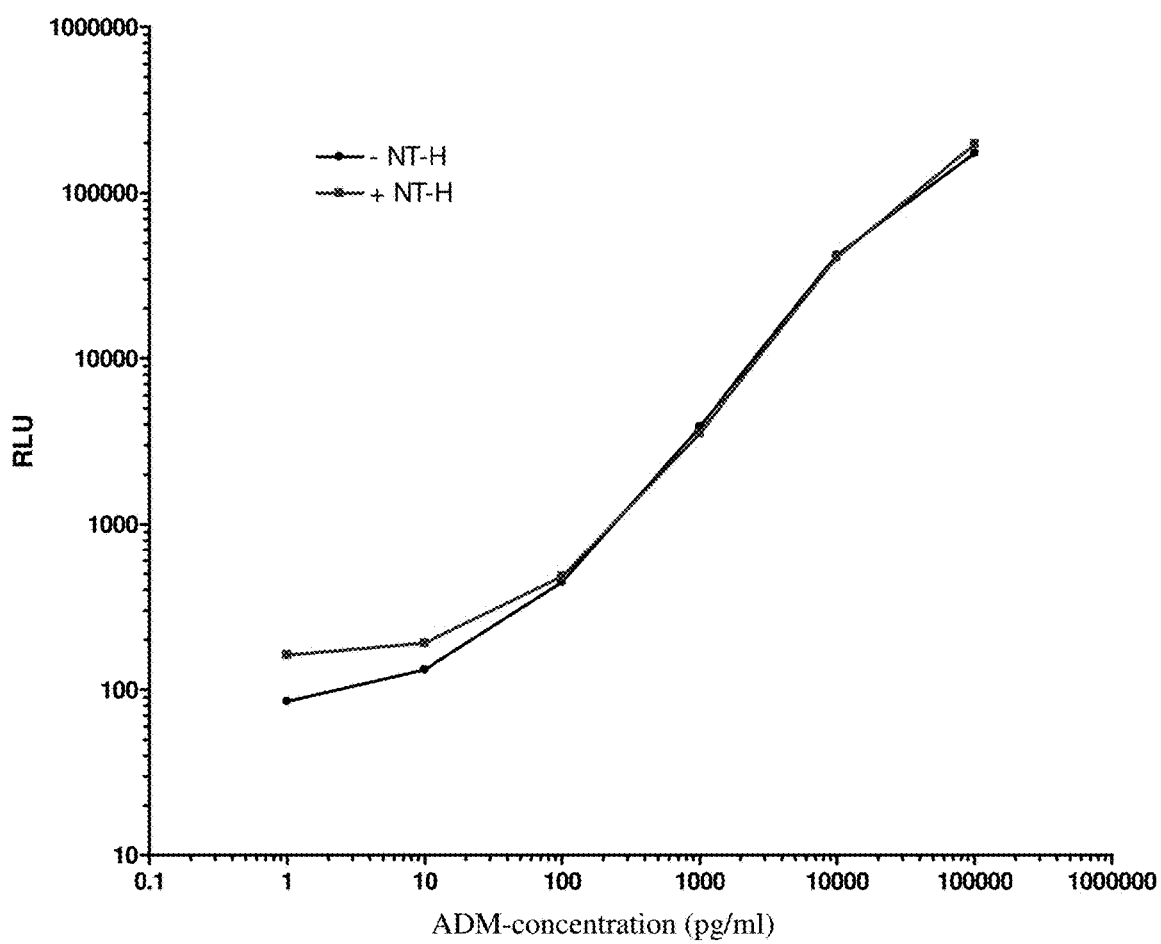

12 Claims, 7 Drawing Sheets
Specification includes a Sequence Listing.

Predicting in-hospital mortality

☐ Results from logistic regression:

| Model | N | Events | Model Chi2 | d.f. | LR p-value | C index [95-CI] |
|---|---|---|---|---|---|---|
| hADM | 101 | 27 | 19.23 | 1 | 0.00001 | 0.737 [0.622,0.852] |
| Apache | 101 | 27 | 19.98 | 1 | 0.00001 | 0.783 [0.681,0.886] |

Predicting in-hospital mortality

- ADM is independent from Apache and provides additional prognostic information:

| | LR $\chi^2$ | d.f. | p value |
|---|---|---|---|
| adding Apache (Apache) to hADM | 7.14 | 1 | 0.0075 |
| adding hADM (hADM) to Apache | 6.39 | 1 | 0.0115 |

- AUC(ADM plus APACHE): 0.799 (vs. 0.783 for APACHE alone)
- Chi²: 26.4 (vs. 20.0 for APACHE)

| Subgroup | Mean | SD | Median | IQR | Q1 | Q3 | Q.95 | Min | Max | n |
|---|---|---|---|---|---|---|---|---|---|---|
| later | 89.623 | 54.570 | 87.220 | 89.102 | 43.87 | 132.972 | 141.618 | 40.27 | 143.78 | 4 |
| never | 66.348 | 73.469 | 48.430 | 40.570 | 31.68 | 72.250 | 154.614 | 14.36 | 592.47 | 79 |
| on Adm | 176.343 | 112.615 | 129.395 | 181.305 | 82.78 | 264.085 | 358.909 | 47.59 | 394.21 | 18 |

Diagonal segments are produced by ties.

SEQUENCE LISTING

```
<160> NUMBER OF SEQ ID NOS: 9

<210> SEQ ID NO 1
<211> LENGTH: 164
<212> TYPE: PRT
<213> ORGANISM: Homo sapiens

<400> SEQUENCE: 1

Ala Arg Leu Asp Val Ala Ser Glu Phe Arg Lys Lys Trp Asn Lys Trp
1               5                   10                  15

Ala Leu Ser Arg Gly Lys Arg Glu Leu Arg Met Ser Ser Ser Tyr Pro
            20                  25                  30

Thr Gly Leu Ala Asp Val Lys Ala Gly Pro Ala Gln Thr Leu Ile Arg
        35                  40                  45

Pro Gln Asp Met Lys Gly Ala Ser Arg Ser Pro Glu Asp Ser Ser Pro
    50                  55                  60
```

```
Asp Ala Ala Arg Ile Arg Val Lys Arg Tyr Arg Gln Ser Met Asn Asn
 65                  70                  75                  80

Phe Gln Gly Leu Arg Ser Phe Gly Cys Arg Phe Gly Thr Cys Thr Val
                 85                  90                  95

Gln Lys Leu Ala His Gln Ile Tyr Gln Phe Thr Asp Lys Asp Lys Asp
            100                 105                 110

Asn Val Ala Pro Arg Ser Lys Ile Ser Pro Gln Gly Tyr Gly Arg Arg
            115                 120                 125

Arg Arg Arg Ser Leu Pro Glu Ala Gly Pro Gly Arg Thr Leu Val Ser
        130                 135                 140

Ser Lys Pro Gln Ala His Gly Ala Pro Ala Pro Pro Ser Gly Ser Ala
145                 150                 155                 160

Pro His Phe Leu

<210> SEQ ID NO 2
<211> LENGTH: 20
<212> TYPE: PRT
<213> ORGANISM: Homo sapiens

<400> SEQUENCE: 2

Ala Arg Leu Asp Val Ala Ser Glu Phe Arg Lys Lys Trp Asn Lys Trp
 1               5                  10                  15

Ala Leu Ser Arg
            20

<210> SEQ ID NO 3
<211> LENGTH: 48
<212> TYPE: PRT
<213> ORGANISM: Homo sapiens

<400> SEQUENCE: 3

Glu Leu Arg Met Ser Ser Ser Tyr Pro Thr Gly Leu Ala Asp Val Lys
 1               5                  10                  15

Ala Gly Pro Ala Gln Thr Leu Ile Arg Pro Gln Asp Met Lys Gly Ala
            20                  25                  30

Ser Arg Ser Pro Glu Asp Ser Ser Pro Asp Ala Ala Arg Ile Arg Val
            35                  40                  45

<210> SEQ ID NO 4
<211> LENGTH: 52
<212> TYPE: PRT
<213> ORGANISM: Homo sapiens

<400> SEQUENCE: 4

Tyr Arg Gln Ser Met Asn Asn Phe Gln Gly Leu Arg Ser Phe Gly Cys
 1               5                  10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
            35                  40                  45

Pro Gln Gly Tyr
        50

<210> SEQ ID NO 5
<211> LENGTH: 53
<212> TYPE: PRT
<213> ORGANISM: Homo sapiens
```

```
<400> SEQUENCE: 5

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
                20                  25                  30

Phe Thr Asp Lys Asp Lys Asp Asn Val Ala Pro Arg Ser Lys Ile Ser
            35                  40                  45

Pro Gln Gly Tyr Gly
        50

<210> SEQ ID NO 6
<211> LENGTH: 38
<212> TYPE: PRT
<213> ORGANISM: Homo sapiens

<400> SEQUENCE: 6

Arg Arg Arg Arg Arg Ser Leu Pro Glu Ala Gly Pro Gly Arg Thr Leu
1               5                   10                  15

Val Ser Ser Lys Pro Gln Ala His Gly Ala Pro Ala Pro Pro Ser Gly
                20                  25                  30

Ser Ala Pro His Phe Leu
        35

<210> SEQ ID NO 7
<211> LENGTH: 16
<212> TYPE: PRT
<213> ORGANISM: Homo sapiens

<400> SEQUENCE: 7

Tyr Arg Gln Ser Met Asn Asn Phe Gln Gly Leu Arg Ser Phe Gly Cys
1               5                   10                  15

<210> SEQ ID NO 8
<211> LENGTH: 12
<212> TYPE: PRT
<213> ORGANISM: Homo sapiens

<400> SEQUENCE: 8

Cys Thr Val Gln Lys Leu Ala His Gln Ile Tyr Gln
1               5                   10

<210> SEQ ID NO 9
<211> LENGTH: 12
<212> TYPE: PRT
<213> ORGANISM: Homo sapiens

<400> SEQUENCE: 9

Cys Ala Pro Arg Ser Lys Ile Ser Pro Gln Gly Tyr
1               5                   10
```

ADRENOMEDULLIN TO GUIDE THERAPY OF BLOOD PRESSURE DECLINE

Subject matter of the present invention is an in vitro method for identifying a subject in need of administration of fluid resuscitation or a vasopressor comprising the following steps:

Determining the level of proADM and/or fragments thereof having at least 6 amino acids in a bodily fluid of said subject Correlating said level with the need of said patient for fluid resuscitation or administration of a vasopressor wherein said patient is identified as having such a need if the level of proADM and/or fragments thereof having at least 6 amino acids in the bodily fluid of said subject is above a threshold.

The peptide adrenomedullin (ADM) was described for the first time in Kitamura et al., (cf. 1; numerical data are based on the attached list of references) as a novel hypotensive peptide comprising 52 amino acids, which had been isolated from a human pheochromocytoma. In the same year, cDNA coding for a precursor peptide comprising 185 amino acids and the complete amino acid sequence of this precursor peptide were also described. The precursor peptide, which comprises, inter alia, a signal sequence of 21 amino acids at the N-terminus, is referred to as "preproadrenomedullin" (pre-proADM). Pre-proADM comprises 185 amino acids. The mature ADM is displayed in SEQ ID No. 4 and ADM-Gly is displayed in SEQ No. 5.

The mature peptide adrenomedullin (ADM) is an amidated peptide which comprises 52 amino acids (SEQ ID No: 4) and which comprises the amino acids 95 to 146 of pre-proADM, from which it is formed by proteolytic cleavage. To date, substantially only a few fragments of the peptide fragments formed in the cleavage of the pre-proADM have been more exactly characterized, in particular the physiologically active peptides adrenomedullin (ADM) and "PAMP", a peptide comprising 20 amino acids (22-41) which follows the 21 amino acids of the signal peptide in pre-proADM. For both ADM and PAMP, physiologically active sub-fragments have furthermore been discovered and investigated in more detail. The discovery and characterization of ADM in 1993 triggered intensive research activity and a flood of publications, the results of which have recently been summarized in various review articles, in the context of the present description, reference being made in particular to the articles to be found in an issue of "Peptides" devoted to ADM (Peptides 22 (2001)), in particular (2) and (3). A further review is (4). In the scientific investigations to date, it has been found, inter alia, that ADM may be regarded as a polyfunctional regulatory peptide. It is released into the circulation in an inactive form extended by glycine (5). There is also a binding protein (6) which is specific for ADM and probably likewise modulates the effect of ADM.

Those physiological effects of ADM as well as of PAMP which are of primary importance in the investigations to date were the effects influencing blood pressure. Thus, ADM is an effective vasodilator, it being possible to associate the hypotensive effect with in particular peptide segments in the C-terminal part of ADM.

It has furthermore been found that the above-mentioned further physiologically active peptide PAMP formed from pre-proADM likewise exhibits a hypotensive effect, even if it appears to have an action mechanism differing from that of ADM (cf. in addition to the above-mentioned review articles (3) and (4) also (7), (8) or (9) and (10)).

It has furthermore been found that the concentrations of ADM which can be measured in the circulation and other biological fluids are, in a number of pathological states, significantly above the concentrations to be found in healthy control persons. Thus, the ADM level in patients with congestive heart failure, myocardial infarction, kidney diseases, hypertensive disorders, Diabetes mellitus, in the acute phase of shock and in sepsis and septic shock are significantly increased, although to different extents. The PAMP concentrations are also increased in some of said pathological states, but the plasma levels are reduced relative to ADM ((3); page 1702).

It is furthermore known that unusually high concentrations of ADM are to be observed in sepsis or in septic shock (cf. (3) and (11), (12), (13), (14) and (15)). The findings are related to the typical hemodynamic changes which are known as typical phenomena of the course of a disease in patients with sepsis and other severe syndromes, such as, for example, SIRS.

Although it is assumed that ADM and PAMP are formed from the same precursor peptide, pre-proADM, in which the amino acid sequences corresponding to these peptides are present as partial peptides in equimolar amounts, the concentrations of ADM or PAMP measurable in biological fluids apparently differ. This is nothing unusual.

Thus, the measurable concentrations of different degradation products of one and the same precursor peptide may be different, for example, because they are the result of different competing degradation pathways which, for example in the case of different pathological states, lead to different fragmentation of a precursor peptide and hence to different degradation products. Certain partial peptides contained in the precursor peptide may be formed as free peptides or may not be formed, and/or different peptides are formed in different ways and in different amounts. Even if only a single degradation pathway is taken for processing a precursor peptide, and hence all degradation products originate from one and the same precursor peptide and must have been formed per se primarily in equimolar amounts, the steady state concentrations of different partial peptides and fragments measurable in biological fluids may be very different, namely, for example, when individual ones thereof are formed at a different rate and/or have different individual stabilities (lifetimes) in the respective biological fluid, or if they are removed from circulation on the basis of different clearance mechanisms and/or at different clearance rates.

Adrenomedullin plays pivotal roles during sepsis development ((16), (17)) and in numerous acute and chronic diseases ((18), (4)).

Several methods have been described to measure circulating levels of ADM: Either ADM directly or indirectly by determining a more stable fragment of its cognate precursor peptide. Very recently a method has been published describing an assay to measure circulating mature ADM (Di Somma S, Magrini L, Travaglino F, Lalle I, Fiotti N, Cervellin G, Avanzi G C, Lupia E, Maisel A, Hein F et al: Opinion paper on innovative approach of biomarkers for infectious diseases and sepsis management in the emergency department. Clinical chemistry and laboratory medicine: CCLM/FESCC 2013: 1-9.)

Other methods to quantify fragments derived from the ADM precursor have been described, e.g. the measurement of MR-proADM (Morgenthaler N G, Struck J, Alonso C, Bergmann A. Clin Chem. 2005 October; 51(10):1823-9.), PAMP (Washimine H, Kitamura K, Ichiki Y, Yamamoto Y, Kangawa K, Matsuo H, Eto T. Biochem Biophys Res Commun. 1994 Jul. 29; 202(2):1081-7.), CT-proADM (EP211552). A commercial assay for the measurement of MR-proADM is available (BRAHMS MR-proADM KRYPTOR; BRAHMS GmbH, Hennigsdorf, Germany) (Clin Biochem. 2009 May; 42(7-8):725-8. doi: 10.1016/j.clinbiochem.2009.01.002. Epub 2009 Jan. 23).

Homogeneous time-resolved fluoroimmunoassay for the measurement of midregional proadrenomedullin in plasma on the fully automated system B.R.A.H.M.S KRYPTOR (Caruhel P, Mazier C, Kunde J, Morgenthaler N G, Darbouret B.). As these peptides are generated in a stoichiometric ratio from the same precursor, their plasma levels are correlated to a certain extent.

Only in a few studies plasma ADM has been measured in patients with systemic inflammation, sepsis, severe sepsis or septic shock, and levels have been correlated with hemodynamic parameters:

In a study by Hirata et al. plasma ADM in septic patients was found to be correlated with heart rate, right arterial pressure, but not with mean arterial pressure (MAP) (Hirata Y, Mitaka C, Sato K, Nagura T, Tsunoda Y, Amaha K, Marumo F: Increased circulating adrenomedullin, a novel vasodilatory peptide, in sepsis. The Journal of clinical endocrinology and metabolism 1996, 81(4):1449-1453).

Nishio et al. reported that increased plasma concentrations of ADM were correlated with relaxation of vascular tone in patients with septic shock (correlation with cardiac index, stroke volume index, heart rate, decrease in diastolic blood pressure, systemic vascular resistance index and pulmonary vascular resistance index), however there was no significant correlation with mean blood pressure [19].

In healthy subjects under exercise a significant negative correlation of plasma ADM and MAP was found [20].

Nothing is known about the association of circulating ADM or related peptide levels as pro-ADM or fragments thereof and the requirements for fluid resuscitation and vasopressors in patients developing shock. This is an unmet medical need as vasopressors are usually given very late when the condition of the patient is very serious. It is an unmet medical need to identify those patients in need of fluid resuscitation and vasopressors before the condition of the patient is very serious. It is an unmet medical need to predict the requirement for fluid resuscitation and vasopressor therapy earlier than by blood pressure measurement applying the cut-off value of 65 mm Hg, as recommended in the guidelines [21]. If blood pressure fells, this leads to diminished oxygen supply, organ dysfunction and death. It is thus an unmet need to early identify patients who are at risk to develop a blood pressure decline. If such patients could be identified earlier, other, e.g. higher cut-off values for mean arterial pressure could be applied to initiate fluid resuscitation and vasopressor therapy. Higher threshold-levels are <70 mm Hg, preferably <75 mm Hg. This means that therapy starts already above 65 mmHg.

Subject matter of the present invention is an in vitro method for identifying a subject in need of fluid resuscitation or administration of a vasopressor comprising the following steps:
Determining the level of proADM and/or fragments thereof having at least 6 amino acids in a bodily fluid of said subject
Correlating said level with the need of said subject or patient for fluid resuscitation or administration of a vasopressor wherein said subject or patient is identified as having such a need if the level of proADM and/or fragments thereof having at least 6 amino acids in the bodily fluid of said subject is above a threshold.

In one embodiment of the methods according to the invention the subject has a mean arterial pressure>65 mm Hg. Further, said subject may have a mean arterial pressure<75 mmg Hg, in another embodiment <70 mmg Hg.

In one embodiment of the invention said method is a method for the early identification of fluid resuscitation or administration of a vasopressor wherein earlier means earlier than by blood pressure measurement applying a cut-off value of 65 mmg Hg or before the blood pressure dropped to 65 mmg Hg.

A bodily fluid according to the present invention is in one particular embodiment a blood sample. A blood sample may be selected from the group comprising whole blood, serum and plasma.

In a specific embodiment of the invention said proADM and/or fragments thereof having at least 6 amino acids is/are selected from the group comprising:

```
                                         SEQ ID No. 1
(proADM): 164 amino acids (22 - 185 of
preproADM)
ARLDVASEF RKKWNKWALS RGKRELRMSS SYPTGLADVK

AGPAQTLIRP QDMKGASRSP EDSSPDAARI RVKRYRQSMN

NFQGLRSFGC RFGTCTVQKL AHQIYQFTDK DKDNVAPRSK

ISPQGYGRRR RRSLPEAGPG RTLVSSKPQ HGAPAPPSGS APHFL

SEQ ID No. 2
(Proadrenomedullin N-20 terminal peptide):
Peptides 22 - 41
ARLDVASEF RKKWNKWALS R SEQ ID No. 3
(MidregionalproAdrenomedullin, MR-proADM):
Peptides45 - 92
ELRMSS SYPTGLADVK AGPAQTLIRP QDMKGASRSP

EDSSPDAARI RV

SEQ ID No. 4
(mature Adrenomedullin (mature ADM); amidated):
Peptides 95 - 146 - CONH2
YRQSMN NFQGLRSFGC RFGTCTVQKL AHQIYQFTDK DKDNVAPRSK

ISPQGY - CONH2

SEQ ID No. 5
(Adrenomedullin 1-52-Gly (ADM 1-52-Gly)):
Peptides 95 - 147
YRQSMN NFQGLRSFGC RFGTCTVQKL AHQIYQFTDK DKDNVAPRSK

ISPQGYG

SEQ ID No. 6
(C-terminal proAdrenomedullin, CT-proADM):
Peptides 148 - 185
RRR RRSLPEAGPG RTLVSSKPQA HGAPAPPSGS APHFL
```

In a specific embodiment of the invention said proADM and/or fragments thereof having at least 6 amino acids is/are selected from the group comprising mature ADM (SEQ ID No. 4) and/or mature ADM 1-52-Gly (SEQ ID No. 5) and MR-proADM (SEQ ID No. 3) and CT-proADM (SEQ ID No. 6).

In a specific embodiment of the invention either the level of mature ADM (SEQ ID No. 4) and/or mature ADM 1-52-Gly (SEQ ID No. 5)—immunoreactivity or the level of MR-proADM (SEQ ID No. 3) immunoreactivity or the level of CT-proADM (SEQ ID No. 6) immunoreactivity is determined and correlated with the need of said patient for fluid resuscitation or administration of a vasopressor wherein said patient is identified as having such a need if the level of mature ADM (SEQ ID No. 4) and/or mature ADM 1-52-Gly (SEQ ID No. 5)—immunoreactivity or the level of MR-proADM (SEQ ID No. 3) immunoreactivity or the level of CT-proADM (SEQ ID No. 6) immunoreactivity in the bodily fluid of said subject is above a threshold.

In a specific embodiment of the invention the level of pro-ADM and/or fragments thereof is determined by using at least one binder selected from the group: a binder that binds to a region comprised within the following sequence of mature ADM (SEQ ID No. 4) and/or mature ADM 1-52-Gly (SEQ ID No. 5) and a second binder that binds to a region comprised within the sequence of mature ADM (SEQ ID NO. 4) and/or mature ADM 1-52-Gly (SEQ ID No. 5).

In a specific embodiment of the invention the level of pro-ADM and/or fragments thereof is determined by using at least one binder selected from the group: a binder that binds to a region comprised within the sequence of MR-proADM (SEQ ID No. 3) and a second binder that binds to a region comprised within the sequence of MR-proADM (SEQ ID No. 3)

In a specific embodiment of the invention the level of pro-ADM and/or fragments thereof is determined by using at least one binder selected from the group: a binder that binds to a region comprised within the sequence of CT-proADM (SEQ ID No. 6) and a second binder that binds to a region comprised within the sequence of CT-pro ADM (SEQ ID No. 6).

In a specific embodiment of the invention an assay is used for determining the level of proADM and/or fragments thereof having at least 6 amino acids wherein the assay sensitivity of said assay is able to quantify the ADM of healthy subjects and is <70 pg/ml, preferably <40 pg/ml and more preferably <10 pg/ml.

In a specific embodiment of the invention said binder exhibits an binding affinity to proADM and/or fragments thereof of at least $10^7$ $M^{-1}$, preferred $10^8$ $M^{-1}$, preferred affinity is greater than $10^9$ $M^{-1}$, most preferred greater than $10^{10}$ $M^{-1}$ A person skilled in the art knows that it may be considered to compensate lower affinity by applying a higher dose of compounds and this measure would not lead out-of-the-scope of the invention.

To determine the affinity of the antibodies to Adrenomedullin, the kinetics of binding of Adrenomedullin to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare), (22).

In a specific embodiment of the invention said binder is selected from the group comprising an antibody or an antibody fragment or a non-Ig scaffold binding to proADM and/or fragments thereof.

In a specific embodiment of the invention an assay is used for determining the level of proADM and/or fragments thereof having at least 6 amino acids wherein such assay is a sandwich assay, preferably a fully automated assay.

In one embodiment of the invention it may be a so-called POC-test (point-of-care) that is a test technology which allows performing the test within less than 1 hour near the patient without the requirement of a fully automated assay system. One example for this technology is the immuno-chromatographic test technology.

In one embodiment of the invention such an assay is a sandwich immunoassay using any kind of detection technology including but not restricted to enzyme label, chemiluminescence label, electrochemiluminescence label, preferably a fully automated assay. In one embodiment of the invention such an assay is an enzyme labeled sandwich assay. Examples of automated or fully automated assay comprise assays that may be used for one of the following systems: Roche Elecsys®, Abbott Architect®, Siemens Centauer®, Brahms Kryptor®, BiomerieuxVidas®, Alere Triage®.

A variety of immunoassays are known and may be used for the assays and methods of the present invention, these include: radioimmunoassays ("RIA"), homogeneous enzyme-multiplied immunoassays ("EMIT"), enzyme linked immunoadsorbent assays ("ELISA"), apoenzyme reactivation immunoassay ("ARIS"), dipstick immunoassays and immuno-chromotography assays.

In a specific embodiment of the invention at least one of said two binders is labeled in order to be detected.

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

In a preferred embodiment said label is selected from the group comprising chemiluminescent label, enzyme label, fluorescence label, radioiodine label.

The assays can be homogenous or heterogeneous assays, competitive and non-competitive assays. In one embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (23).

In another embodiment the assay comprises two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows for the detection of the formed sandwich complexes in the solution comprising the sample.

In another embodiment, said labeling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluorescein isothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidium bromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in (24). Preferred chemiluminescent dyes are acridinium esters.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ M$^{-1}$.

In the context of the present invention, "binder molecules" are molecules which may be used to bind target molecules or molecules of interest, i.e. analytes (i.e. in the context of the present invention PCT and fragments thereof), from a sample. Binder molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, binder molecules may for instance be selected from the group comprising a nucleic acid molecule, a carbohydrate molecule, a PNA molecule, a protein, an antibody, a peptide or a glycoprotein. Preferably, the binder molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

Chemiluminescent label may be acridinium ester label, steroid labels involving isoluminol labels and the like.

Enzyme labels may be lactate dehydrogenase (LDH), creatine kinase (CPK), alkaline phosphatase, aspartate aminotransferace (AST), alanine aminotransferace (ALT), acid phosphatase, glucose-6-phosphate dehydrogenase and so on.

In one embodiment of the invention at least one of said two binders is bound to a solid phase as magnetic particles, and polystyrene surfaces.

In a specific embodiment of the invention at least one of said two binders is bound to a solid phase.

In one embodiment of the invention the concentration of ADM or fragments thereof measured in the sample is in the range between 10-500 pg/ml in plasma or blood.

The ADM levels of the present invention or proADM levels or fragments thereof, respectively, have been determined with the described ADM assay, as outlined in the examples (or proADM or fragments thereof assays, respectively). The above mentioned values might be different in other ADM assays (or proADM or fragments thereof assays, respectively), depending upon their way of calibration. The above mentioned values shall apply for such differently calibrated ADM assays accordingly, taking into account the differences in calibration. ADM assays could be calibrated by correlation and adjustment via their normal ranges (healthy population). (or proADM or fragments thereof assays, respectively) Alternatively, commercially available control samples could be used for adjustment of different calibrations (ICI Diagnostics, Berlin, Germany).

With the described ADM assay, the median of a normal population has been determined to be 24.7 pg/mL.

In a specific embodiment of the invention a threshold for plasma ADM of 90 pg/ml, preferably 70 pg/ml is applied.

In a specific embodiment of the invention a threshold for plasma MR-proADM of 0.9 nmol/L, preferably 0.7 nmol/L is applied In a specific embodiment of the invention a threshold for plasma CT-proADM of 1.0 nmol/L, preferably 0.8 nmol/L is applied.

If the level of plasma ADM or plasma MR-proADM or plasma CT-proADM is above said threshold the person might be in need of treatment with a vasopressor.

In a specific embodiment of the invention said sample is selected from the group comprising human citrate plasma, heparin plasma, EDTA plasma, whole blood.

The subject that may be in need of fluid resuscitation or treatment with a vasopressor may suffer from a condition selected from the group comprising: patients at risk to develop physiological shock states, as described in more detail below, but also infections, SIRS, sepsis, heart failure, cardiopulmonary arrest, postoperative cardiac surgery, right ventricular infarction, bradyarrhythmias, polytrauma, burns, kidney injury.

This type of shock can be caused by:
Severe bleeding.
Pulmonary embolus (a blood clot in the lungs).
Severe vomiting and diarrhoea.
Spinal injury.
Poisoning.

There are also specific types of physiological shock, with very particular symptoms.

Cardiogenic Shock:
Cardiogenic shock occurs when the heart is severely damaged—by a major heart attack, for example—and is no longer able to pump blood around the body properly, causing very low blood pressure. This develops after about eight percent of heart attacks. It can be difficult to treat, but drugs may be given to make the heart beat stronger. This may be enough to bring someone through the worst until the heart can mend itself, but cardiogenic shock is still fatal in as many as eight out of ten cases. New treatments to 'revascularise' or restore blood flow to the heart muscle are improving survival rates.

Septic Shock:
This occurs when an overwhelming bacterial infection causes blood pressure to drop. It's fatal in more than 50% of cases. Although it's caused by bacterial infection, treating septic shock with antibiotics is far from simple, because the bacteria release massive amounts of toxin when they are killed off, which initially makes the shock worse. It must always be treated in hospital where the correct drugs and fluid support can be given. One type of septic shock is toxic shock syndrome—a rare but severe illness caused by certain strains of the bacteria *Staphylococcus aureus*.

Anaphylactic Shock:

Anaphylactic shock is a severe allergic reaction. Common triggers include bee and wasp stings, nuts, shellfish, eggs, latex and certain medications, including penicillin. Symptoms include:

Burning and swelling of the lips and tongue.
Difficulty breathing (like in an asthma attack).
Red, itchy or blistered skin, sneezing.
Watery eyes.
Nausea.
Anxiety.

Anaphylaxis requires urgent treatment in hospital. People at risk should always carry an emergency anaphylaxis treatment kit that includes adrenaline.

Sepsis and its escalated forms (severe sepsis, septic shock) continue to be a major medical problem, with mortality rates ranging from 30 to 70%. Despite advances in supportive care, each year 750,000 people develop sepsis and 225,000 die in the United States alone, and the incidence of sepsis is rising at rates between 1.5% and 8% per year [4-6]. In order to save the life of a septic patient, it is essential to first timely fight the infectious stimulus by antibiotics or other measures, and second, to timely recognize escalation of the situation, e.g. when severe sepsis proceeds to septic shock, because only then suitable vasopressor therapy can be initiated early. Any delay would increase the risk of the patient to die.

The conditions under which it is recommended to initiate a fluid resuscitation or vasopressor/inotrope therapy in patients progressing to septic shock are described in the guidelines of the Surviving Sepsis Campaign [3]: It is recommended to apply vasopressors for hypotension that does not respond to initial fluid resuscitation to maintain a mean arterial pressure (MAP) of ≥65 mm Hg. The guideline also talks about which vasopressor/inotrope to apply preferentially when. The current consensus view is: Norepinephrine as the first choice vasopressor. Epinephrine (added to and potentially substituted for norepinephrine) when an additional agent is needed to maintain adequate blood pressure. Vasopressin 0.03 units/minute can be added to norepinephrine (NE) with intent of either raising MAP or decreasing NE dosage (UG). In general, currently used vasopressors and inotropes in clinical practice are [7, 8]:

Catecholamines (Dopamine, Dobutamine, Norepinephrine, Epinephrine, Isoproterenol, Phenylephrine), Phosphodiesterase III inhibitors (Milrinone, Amrinone), Vasopressin, Levosimendan.

Additionally, other vasoactive compounds are under development, such as for instance Selepressin, a selective vasopressin V1a receptor agonist [9] and anti-Adrenomedullin antibodies.

Other compounds have been investigated, but clinical data available for these treatments are sparse, and fairly equivocal results of these approaches have been obtained in larger trials [10]. These are inhibitors of ATP-dependent K+-channels (glibenclamide; [11, 12]) of NOS ($N^G$-monomethyl-L-arginine [13, 14]) and of cGMP (methylene blue [15, 16]).

Vasopressors and inotropes are clinically applied to treat and prevent various physiological shock types, but also cardiovascular diseases (congestive heart failure, cardiopulmonary arrest, postoperative cardiac surgery, right ventricular infarction, bradyarrhythmias) [7]

Since blood pressure is always monitored in patients that present in a critical condition, from a clinical point of view, patients with values above the respective thresholds e.g. high ADM (>70 pg/ml) without vasopressor need at presentation should be vasopressor treated by adapting the points of decision from <66 mmHg MAP to e.g. <75 mmHg aiming earlier support of circulation to protect patient from low blood pressure associated organ dysfunctions and subsequent high mortality. Using this rule for patients>70 pg/ml ADM and treating with vasopressors at MAP<=75 mmHg, patients (Group 3) would be treated in average 1.6 days before standard of care treatment (<=66 mmHg).

Thus, in a specific embodiment of the present invention said patient is identified as having a need of administration of a vasopressor if the level of proADM and/or fragments thereof having at least 6 amino acids in the bodily fluid of said subject is above a threshold and if the patient has a </=75 mmHg MAP but preferably >66 mmHg, more preferably >70 mmHg MAP.

In a specific embodiment of the invention a threshold for plasma ADM of 90 pg/ml, preferably 70 pg/ml is applied and/or the patient has a <=/75 mmHg MAP but preferably >66 mmHg, more preferably >70 mmHg MAP.

In a specific embodiment of the invention a threshold for plasma MR-proADM of 0.9 nmol/L, preferably 0.7 nmol/L is applied and/or the patient has a </=75 mmHg MAP but preferably >66 mmHg, more preferably >70 mmHg MAP.

In an specific embodiment of the invention a threshold for plasma CT proADM of 1.0 nmol/L preferably 0.8 nmol/L is applied and/or the patient has a </=75 mmHg MAP but preferably >66 mmHg, more preferably >70 mmHg MAP.

If the level of plasma ADM or plasma MR-proADM or plasma CT proADM is above said threshold and/or if the patient has a </=75 mmHg MAP but preferably >66 mmHg, more preferably >70 mmHg MAP the person might be in need of treatment with a vasopressor.

Fluid replacement or fluid resuscitation is the medical practice of replenishing bodily fluid lost through sweating, bleeding, fluid shifts or other pathologic processes as above described. Fluids can be replaced via oral administration (drinking), intravenous administration, rectally, or by hypodermoclysis, the direct injection of fluid into the subcutaneous tissue. Fluids administered by the oral and hypodermic routes are absorbed more slowly than those given intravenously. Oral rehydration therapy (ORT) is a simple treatment for dehydration associated with diarrhea, particularly gastroenteritis/gastroenteropathy, such as that caused by cholera or rotavirus. ORT consists of a solution of salts and sugars which is taken by mouth.

In severe dehydration, intravenous fluid replacement is preferred, and may be lifesaving. It is especially useful where there is depletion of fluid both in the intracellular space and the vascular spaces.

Fluid replacement is also indicated in fluid depletion due to any of the above described conditions.

An antibody according to the present invention is a protein including one or more polypeptides substantially encoded by immunoglobulin genes that specifically binds an antigen. The recognized immunoglobulin genes include the kappa, lambda, alpha (IgA), gamma ($IgG_1$, $IgG_2$, $IgG_3$, $IgG_4$), delta (IgD), epsilon (IgE) and mu (IgM) constant region genes, as well as the myriad immunoglobulin variable region genes. Full-length immunoglobulin light chains are generally about 25 Kd or 214 amino acids in length. Full-length immunoglobulin heavy chains are generally about 50 Kd or 446 amino acid in length.

Light chains are encoded by a variable region gene at the NH2-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and (Fab')$_2$, as well as bifunctional hybrid antibodies and single chains (e.g., Lanzavecchia et al., *Eur. J. Immunol.* 17:105, 1987; Huston et al., *Proc. Natl. Acad. Sci. U.S.A.*, 85:5879-5883, 1988; Bird et al., *Science* 242:423-426, 1988; Hood et al., *Immunology*, Benjamin, N.Y., 2nd ed., 1984; Hunkapiller and Hood, *Nature* 323:15-16, 1986). An immunoglobulin light or heavy chain variable region includes a framework region interrupted by three hypervariable regions, also called complementarity determining regions (CDR's) (see, *Sequences of Proteins of Immunological Interest*, E. Kabat et al., U.S. Department of Health and Human Services, 1983). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al., PCT Publication No. WO92/001047; and Winter, PCT Publication No. WO92/20791), or selected from a human combinatorial monoclonal antibody library (see the Morphosys website). Human antibodies can also be prepared by using transgenic animals carrying a human immunoglobulin gene (for example, see Lonberg et al., PCT Publication No. WO93/12227; and Kucherlapati, PCT Publication No. WO91/10741).

Thus, the antibody may have the formats known in the art. Examples are human antibodies, monoclonal antibodies, humanized antibodies, chimeric antibodies, CDR-grafted antibodies. In a preferred embodiment antibodies according to the present invention are recombinantly produced antibodies as e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines and numerous others.

In addition to antibodies other biopolymer scaffolds are well known in the art to complex a target molecule and have been used for the generation of highly target specific biopolymers. Examples are aptamers, spiegelmers, anticalins and conotoxins.

In a preferred embodiment the antibody format is selected from the group comprising Fv fragment, scFv fragment, Fab fragment, scFab fragment, (Fab)2 fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is the scFab format.

Non-Ig scaffolds may be protein scaffolds and may be used as antibody mimics as they are capable to bind to ligands or antigenes. Non-Ig scaffolds may be selected from the group comprising tetranectin-based non-Ig scaffolds (e.g. described in US 2010/0028995), fibronectin scaffolds (e.g. described in EP 1266 025; lipocalin-based scaffolds ((e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microproteins, preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and Kunitz domain based scaffolds (e.g. described in EP 1941867).

In one embodiment of the invention antibodies according to the present invention may be produced as follows:

A Balb/c mouse was immunized with ADM-100 µg Peptide-BSA-Conjugate at day 0 and 14 (emulsified in 100 µl complete Freund's adjuvant) and 50 µg at day 21 and 28 (in 100 µl incomplete Freund's adjuvant). Three days before the fusion experiment was performed, the animal received 50 µg of the conjugate dissolved in 100 µl saline, given as one intraperitoneal and one intravenous injection.

Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting, the selected cultures were cloned and recloned using the limiting-dilution technique and the isotypes were determined (see also Lane, R. D. (1985). A short-duration polyethylene glycol fusion technique for increasing production of monoclonal antibody-secreting hybridomas. J. Immunol. Meth. 81: 223-228; Ziegler, B. et al. (1996) Glutamate decarboxylase (GAD) is not detectable on the surface of rat islet cells examined by cytofluorometry and complement-dependent antibody-mediated cytotoxicity of monoclonal GAD antibodies, Horm. Metab. Res. 28: 11-15).

Antibodies may be produced by means of phage display according to the following procedure:

The human naive antibody gene libraries HAL7/8 were used for the isolation of recombinant single chain F-Variable domains (scFv) against adrenomedullin peptide. The antibody gene libraries were screened with a panning strategy comprising the use of peptides containing a biotin tag linked via two different spacers to the adrenomedullin peptide sequence. A mix of panning rounds using non-specifically bound antigen and streptavidin bound antigen were used to minimize background of non-specific binders. The eluted phages from the third round of panning have been used for the generation of monoclonal scFv expressing *E. coli* strains. Supernatant from the cultivation of these clonal strains has been directly used for an antigen ELISA testing (see Hust, M., Meyer, T., Voedisch, B., Rülker, T., Thie, H., El-Ghezal, A., Kirsch, M. I., Schütte, M., Helmsing, S., Meier, D., Schirrmann, T., Dübel, S., 2011. A human scFv antibody generation pipeline for proteome research. Journal of Biotechnology 152, 159-170; Schütte, M., Thullier, P., Pelat, T., Wezler, X., Rosenstock, P., Hinz, D., Kirsch, M. I., Hasenberg, M., Frank, R., Schirrmann, T., Gunzer, M., Hust, M., Dübel, S., 2009. Identification of a putative Crf splice variant and generation of recombinant antibodies for the specific detection of *Aspergillus fumigatus*. PLoS One 4, e6625).

Humanization of murine antibodies may be conducted according to the following procedure: For humanization of an antibody of murine origin the antibody sequence is analyzed for the structural interaction of framework regions (FR) with the complementary determining regions (CDR) and the antigen. Based on structural modeling an appropriate FR of human origin is selected and the murine CDR sequences are transplanted into the human FR. Variations in the amino acid sequence of the CDRs or FRs may be introduced to regain structural interactions, which were abolished by the species switch for the FR sequences. This recovery of structural interactions may be achieved by random approach using phage display libraries or via directed approach guided by molecular modeling (see Almagro J C, Fransson J., 2008. Humanization of antibodies. Front Biosci. 2008 Jan. 1; 13:1619-33).

Another subject matter of the present invention is a vasopressor for use in treatment of a subject in need of fluid resuscitation or administration of a vasopressor wherein said subject is identified according to any of the above described in vitro methods including all embodiments of said in vitro methods.

FIGURE DESCRIPTION

FIG. 1 shows a typical ADM dose/signal curve. And an ADM dose signal curve in the presence of 100 µg/mL antibody NT-H.

Figure 2:
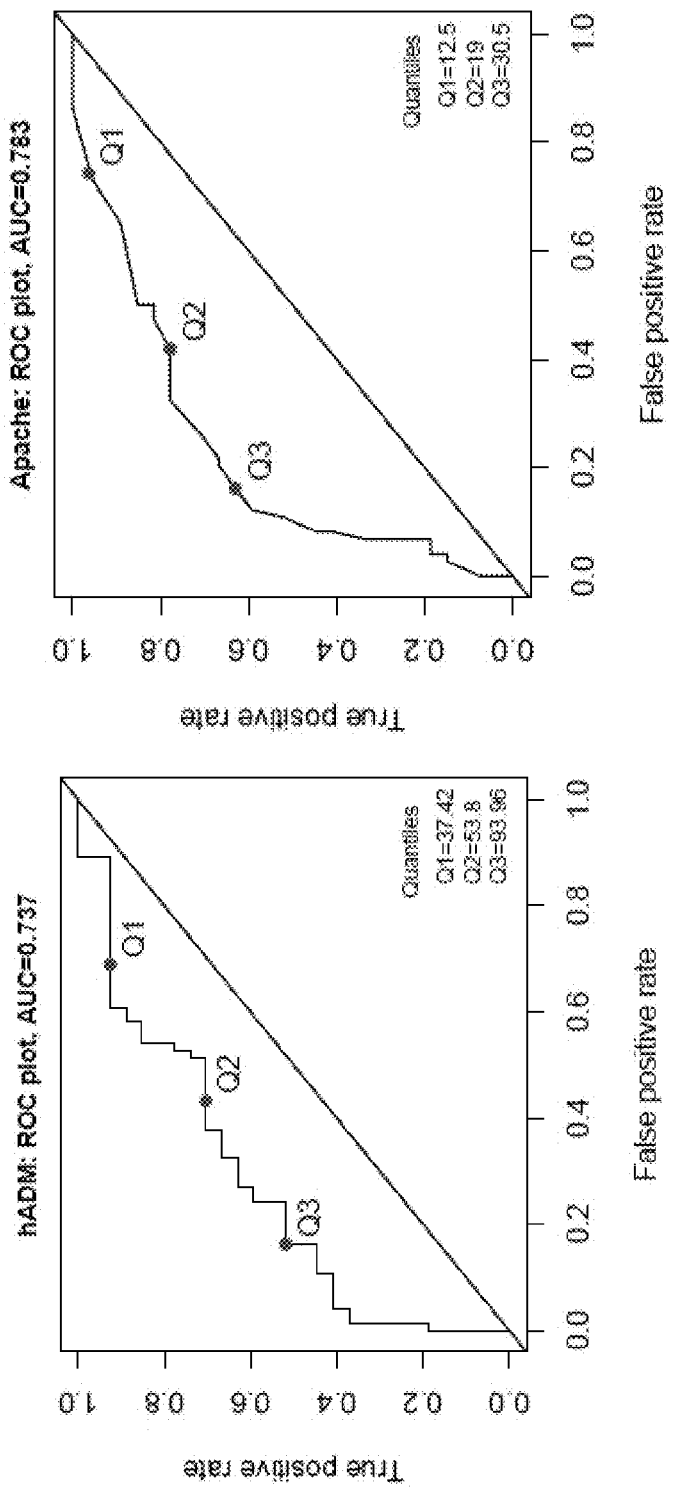

FIG. 2 Predicting in-hospital mortality—Results from logistic regression

Figure 3:
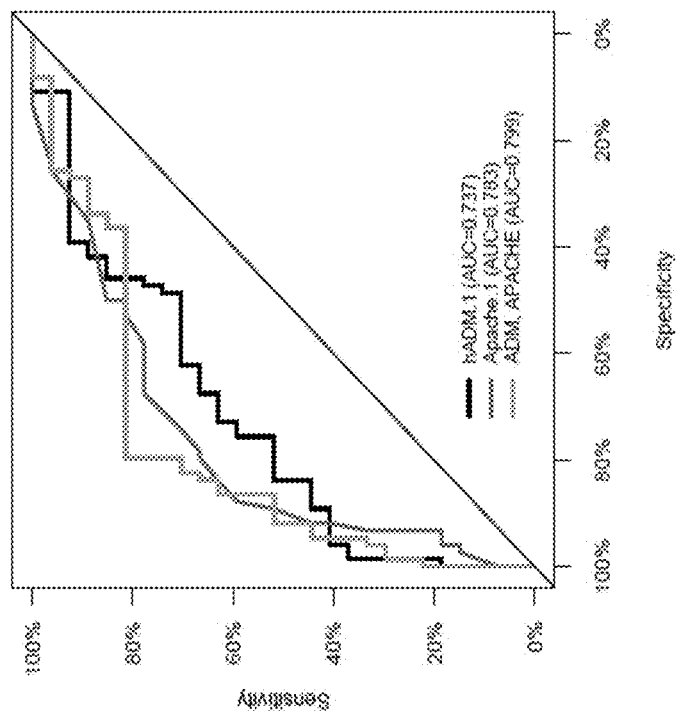
Figure 4:
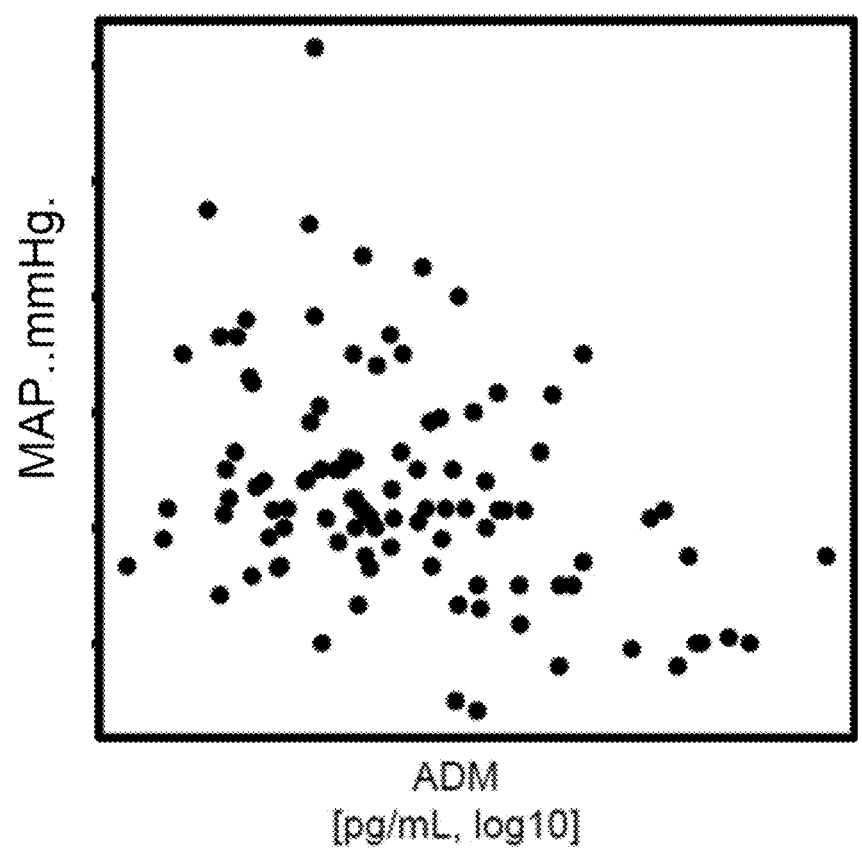

FIG. 3 Predicting in-hospital mortality—ADM is independent from Apache and provides additional prognostic information FIG. 4 Mean arterial pressure depending on plasma ADM levels. Scatter-plot and correlation coefficient are shown for values obtained from patients at admission. Statistical significance was $p<0.0001$.

Figure 5:
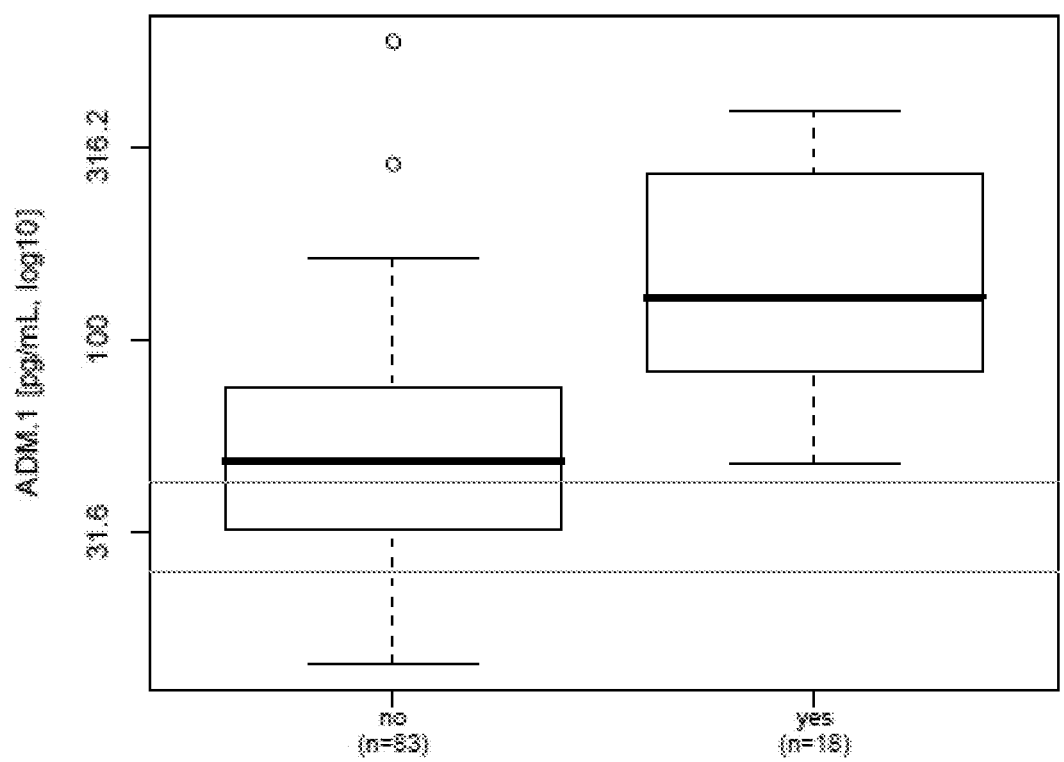

FIG. 5 Adrenomedullin concentrations in patients at admission requiring vasopressor therapy vs patients not requiring vasopressor therapy. The difference between the two groups was statistically significant ($p<0.0001$).

Figure 6:
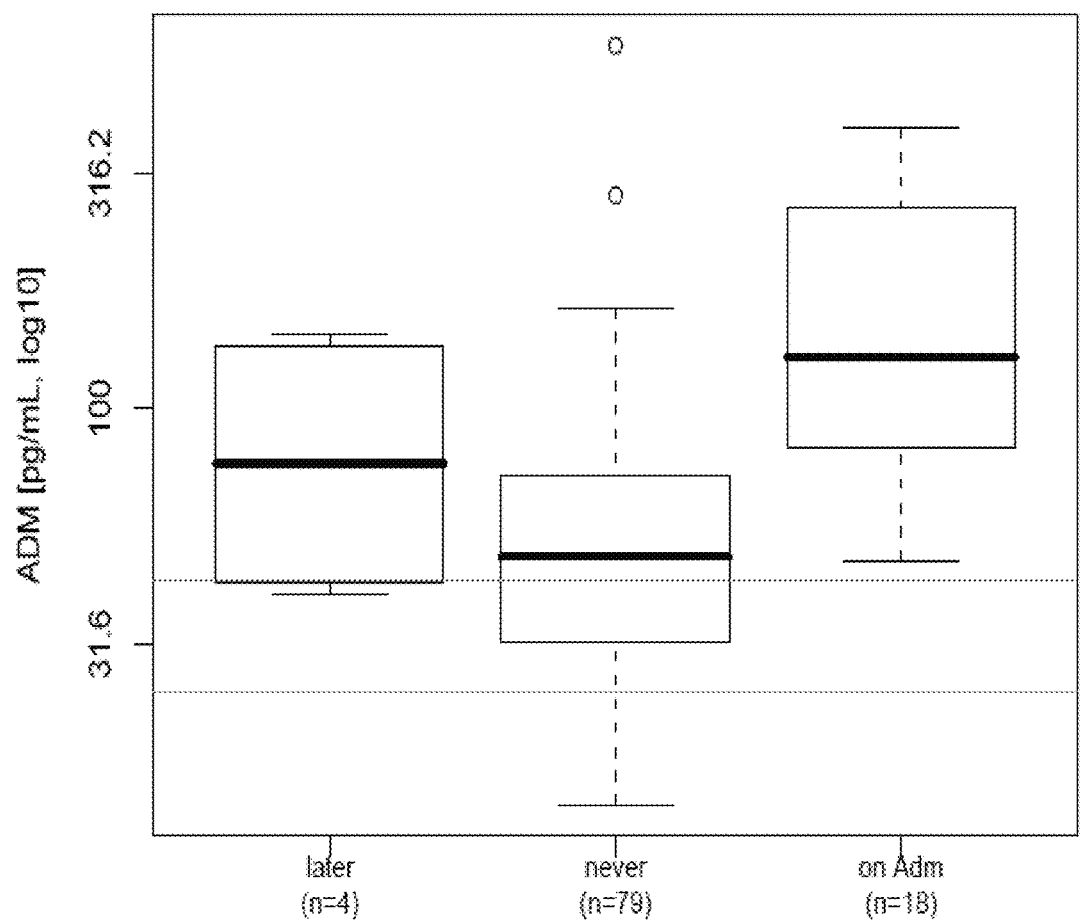

FIG. 6 ADM concentrations of patients at admission, who were treated with vasopressors on admission ("on ADM"), who did not require vasopressor therapy within the first four days after admission ("never"), and who required vasopressor therapy within the first four days after admission, but not on the day of admission ("later"). In the graph, the normal range of ADM concentrations is indicated.

Figure 7:
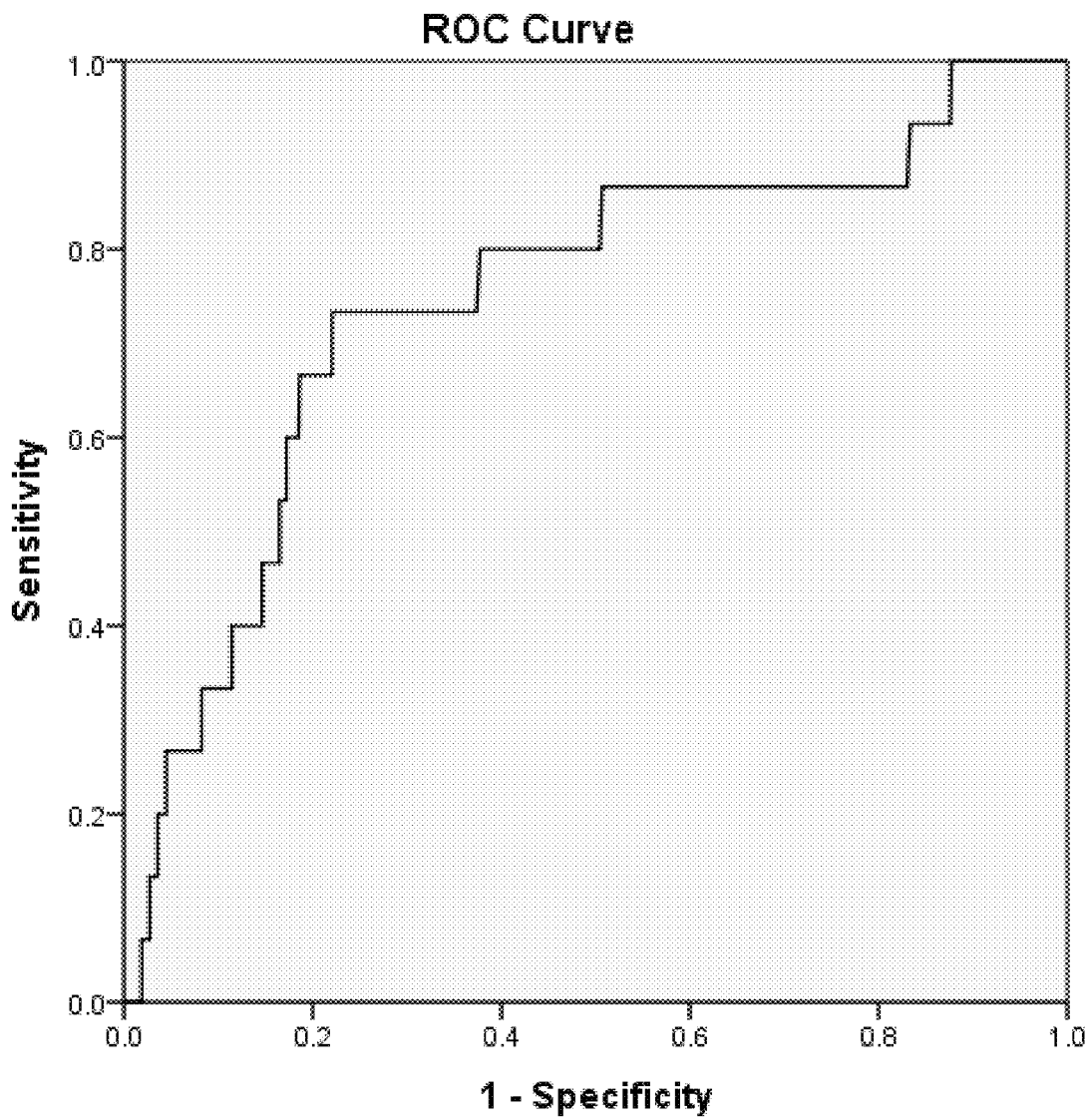

FIG. 7 Receiver Operator Characteristics (ROC) curve for ADM concentrations of acute heart failure patients requiring (sensitivity) and not requiring (specificity) vasopressor therapy. The area under the curve was 0.75 ($p<0.0001$).

EXAMPLE 1

Generation of Antibodies and Determination of Their Affinity Constants

We developed mouse monoclonal antibodies binding to the N-terminal, mid-regional and C-terminal part of ADM and their affinity constants were determined (table 1).

Peptides for Immunization

Peptides were supplied by JPT Peptide Technologies GmbH (Berlin, Germany). Peptides were coupled to BSA using the Sulfo-SMCC crosslinking method. The crosslinking procedure was performed according the manufacturers instructions (Thermo Fisher/Pierce). The murine antibodies were generated according to the following method:

A Balb/c mouse was immunized with 100 µg Peptide-BSA-Conjugate at day 0 and 14 (emulsified in 100 µl complete Freund's adjuvant) and 50 µg at day 21 and 28 (in 100 µl incomplete Freund's adjuvant). Three days before the fusion experiment was performed, the animal received 50 µg of the conjugate dissolved in 100 µl saline, given as one intraperitoneal and one intra venous injection.

Splenocytes from the immunized mouse and cells of the myeloma cell line SP2/0 were fused with 1 ml 50% polyethylene glycol for 30 s at 37° C. After washing, the cells were seeded in 96-well cell culture plates. Hybrid clones were selected by growing in HAT medium [RPMI 1640 culture medium supplemented with 20% fetal calf serum and HAT-Supplement]. After two weeks the HAT medium is replaced with HT Medium for three passages followed by returning to the normal cell culture medium.

The cell culture supernatants were primary screened for antigen specific IgG antibodies three weeks after fusion. The positive tested microcultures were transferred into 24-well plates for propagation. After retesting the selected cultures were cloned and recloned using the limiting-dilution technique and the isotypes were determined.

(Lane, R. D. "A short-duration polyethylene glycol fusion technique for increasing production of monoclonal antibody-secreting hybridomas", J. Immunol. Meth. 81: 223-228; (1985), Ziegler, B. et al. "Glutamate decarboxylase (GAD) is not detectable on the surface of rat islet cells examined by cytofluorometry and complement-dependent antibody-mediated cytotoxicity of monoclonal GAD antibodies", Horm. Metab. Res. 28: 11-15, (1996)).

TABLE 1

| Antigen/Immunogen | ADM Region | Designation | Affinity constants Kd (M-1) |
|---|---|---|---|
| YRQSMNNFQGLRSFGC | 1-16 | NT-ADM | $1.6 \times 10^9$ |
| CTVQKLAHQIYQ | 21-32 | MR-ADM | $2 \times 10^9$ |
| CAPRSKISPQGY-NH2 | C-42-52 | CT-ADM | $1.1 \times 10^9$ |

Monoclonal Antibody Production

Antibodies were produced via standard antibody production methods (Marx et al, Monoclonal Antibody Production, ATLA 25, 121, 1997) and purified via Protein A. The antibody purities were >95% based on SDS gel electrophoresis analysis.

Affinity Constants

To determine the affinity of the antibodies to Adrenomedullin, the kinetics of binding of Adrenomedullin to immobilized antibody was determined by means of label-free surface plasmon resonance using a Biacore 2000 system (GE Healthcare Europe GmbH, Freiburg, Germany). Reversible immobilization of the antibodies was performed using an anti-mouse Fc antibody covalently coupled in high density to a CM5 sensor surface according to the manufacturer's instructions (mouse antibody capture kit; GE Healthcare).

Labelling procedure (tracer): 100 ug (100 ul) of antibody (1 mg/ml in PBS, pH 7.4) was mixed with 10 ul Akridinium NHS-ester (1 mg/ml in acetonitrile, InVent GmbH, Germany) (57) and incubated for 20 min at room temperature. Labelled CT-H was purified by Gel-filtration HPLC on Bio-Sil® SEC 400-5 (Bio-Rad Laboratories, Inc., USA) The purified labeled antibody was diluted in (300 mmol/L potassium phosphate, 100 mmol/L NaCl, 10 mmol/L Na-EDTA, 5 g/L Bovine Serum Albumin, pH 7.0). The final concentration was approx. 800.000 relative light units (RLU) of labelled compound (approx. 20 ng labeled antibody) per 200 µL. Akridinium ester chemiluminescence was measured by using an AutoLumat LB 953 (Berthold Technologies GmbH & Co. KG).

Solid phase: Polystyrene tubes (Greiner Bio-One International AG, Austria) were coated (18 h at room temperature) with antibody ((1.5 µg antibody/0.3 mL 100 mmol/L NaCl, 50 mmol/L TRIS/HCl, pH 7.8). After blocking with 5% bovine serum albumine, the tubes were washed with PBS, pH 7.4 and vacuum dried.

Calibrators:
Synthetic human ADM (Bachem, Switzerland) was linearly diluted using 50 mM Tris/HCl, 250 mM NaCl, 0.2% Triton X-100, 0.5% BSA, 20 tabs/L Protease cOmplete Protease Inhibitor Cocktail Tablets (Roche AG); pH 7.8. Calibrators were stored at −20° C. before use.

EXAMPLE 2

Determination of the Antibody Combination that Yields High Signal/Noise Ratios

ADM Immunoassay:
50 ul of sample (or calibrator) was pipetted into coated tubes, after adding labeled second antibody (200 ul), the tubes were incubated for 2 h at room temperature. Unbound tracer was removed by washing 5 times (each 1 ml) with washing solution (20 mM PBS, pH 7.4, 0.1% Triton X-100).

Tube-bound chemiluminescence was measured by using the LB 953

All antibodies were used in a sandwich immunoassay as coated tube and labeled antibody and combined in the following variations (table 2):

Incubation was performed as described under hADM-Immunoassay. Results are given in ratio of specific signal (at 10 ng/ml ADM)/background (sample without ADM) signal.

TABLE 2

| Signal/ noise ratio | NT-ADM tracer | MR-ADM tracer | CT-ADM tracer |
|---|---|---|---|
| NT-ADM | / | 195 | 241 |
| MRADM | 204 | / | 904 |
| CT-ADM | 260 | 871 | / |

Surprisingly, we found the combination of MR-ADM and CT-ADM as combination for highest signal/noise ratio.

Subsequently, we used this antibody-combination for further investigations. We used MR-ADM as solid phase antibody and CT-ADM as labeled antibody. A typical dose/signal curve is shown in FIG. 1. The analytical sensitivity (average of 10 runs, ADM-free sample+2SD) of the assay was 2 pg ADM/ml.

EXAMPLE 3

Stability of Human Adrenomedullin:
Human ADM was diluted in human Citrate plasma (n=5, final concentration 10 ng ADM/ml) and incubated at 24° C. At selected time points, aliquots were frozen at −20° C. Immediately after thawing the samples hADM was quantified by using the hADM immunoassay described above.

Table 3 shows the stability of hADM in human plasma at 24° C.

| Time (h) | Average ADM recovery (N = 5) | Relative loss of immune reactivity | Loss of immune reactivity %/h |
|---|---|---|---|
| 0 | 100 | / | / |
| 2 | 99.2 | 0.8 | 0.4 |
| 4 | 96.4 | 3.6 | 0.8 |

-continued

| Time (h) | Average ADM recovery (N = 5) | Relative loss of immune reactivity | Loss of immune reactivity %/h |
|---|---|---|---|
| 8 | 88.2 | 11.8 | 1.5 |
|   |   |   | Average: 0.9%/h |

Surprisingly, using the antibody-combinations MR-ADM and CT-ADM in a sandwich immune assay, the preanalytical stability of the analyte is high (only 0.9%/h average loss of immune reactivity). In contrast, using other assay methods, a plasma half life of only 22 min was reported (Hinson 2000). Since the time from taking sample to analysis in hospital routine is less than 2 h, the used ADM detection method is suitable for routine diagnosis. It is remarkable, that any non routine additives to samples (like Aprotinin, (20)) are not needed to reach acceptable ADM-immune reactivity stabilities.

EXAMPLE 4

Reproducibility of Calibrator-Preparations.

We found a high variation of results, preparing calibrators for ADM assays (average CV 8.5%, see table 4). This may be due to high adsorption of hADM to plastic and glass surfaces (see also (58)). This effect was only slightly reduced by adding detergents (up to 1% Triton X 100 or 1% Tween 20), protein (up to 5% BSA) and high ionic strenghth (up to 1M NaCl) or combinations thereof. Surprisingly, if a surplus of anti ADM antibody (10 ug/ml) is added to the calibrator dilution buffer, the recovery and reproducibility of ADM assay calibrator-preparations was substantially improved to <1% of inter preparation CV (table 4).

Fortunately, the presence of N-terminal antibodies did not affect the ADM-signal generated by the combination of MR- and C-terminal antibodies (FIG. 1).

TABLE 4

| calibrator | In the presence of NT-ADM antibody (10 ug/ml) | Inter preparation CV (%) | Without antibody | Inter preparation CV (%) |
|---|---|---|---|---|
| 100 ng/ml | 3453 s/n-r | 0.9 | 2842 s/n-r | 2.8 |
| 10 ng/ml | 1946 s/n-r | 0.8 | 1050 s/n-r | 7.9 |
| 1 ng/ml | 179 s/n-r | 1.1 | 77 s/n-r | 14.8 |
|   |   | Average: 0.93 |   | Average: 8.5 |

Inter Preparation Variation of Calibrators.

ADM assay calibrators were prepared as described above with and without 10 ug/ml of NT-ADM-antibody. Coefficients of variation are given from 5 independent preparation runs. The calibrators were measured using the ADM assay described above. s/n-r=signal to noise ratio.

For all following studies, we used an ADM assay, based on calibrators, prepared in the presence of 10 ug/ml of NT-ADM antibody and 10 ug/ml of NT-ADM antibody as supplement in the tracer buffer.

EXAMPLE 5

Sensitivity

The goal of assay sensitivity was to completely cover the ADM concentration of healthy subjects.

ADM Concentration in Healthy Subjects:

Healthy subjects (n=100, average age 56 years) were measured using the ADM assay. The median value was 24.7 pg/ml, the lowest value 11 pg/ml and the $99^{th}$ percentile 43 pg/ml. Since the assay sensitivity was 2 pg/ml, 100% of all healthy subjects were detectable using the described ADM assay.

A commercial Assay was used to measure MR-proADM (BRAHMS MR-proADM KRYPTOR) (BRAHMS GmbH, Hennigsdorf, Germany) (ClinBiochem. 2009 May; 42(7-8): 725-8. doi: 10.1016/j.clinbiochem.2009.01.002. Epub 2009 Jan. 23.

Homogeneous time-resolved fluoroimmunoassay for the measurement of midregional proadrenomedullin in plasma on the fully automated system B.R.A.H.M.S KRYPTOR. Caruhel P, Mazier C, Kunde J, Morgenthaler N G, Darbouret B.)

EXAMPLE 6

Clinical Study

101 ED patients fulfilling the definition of sepsis (Dellinger R P, Levy M M, Carlet J M, Bion J, Parker M M, Jaeschke R, Reinhart K, Angus D C, Brun-Buisson C, Beale R et al: Surviving Sepsis Campaign: international guidelines for management of severe sepsis and septic shock: 2008. Critical care medicine 2008, 36(1):296-327) were subsequently hospitalized (average 5 days of hospitalization) and received a standard of care treatment. EDTA-plasma was generated from day 1 (ED presentation) and one sample each day during hospital stay. The time to freeze samples for later ADM-measurement was less than 4 h.

Patient characteristics are summarized in table 5

TABLE 5

| Variable | all (n = 101) | in hospitaldeaths (n = 27) | discharged (n = 74) | p-value |
|---|---|---|---|---|
| Demographics | | | | |
| Gender - male | 60 (60) | 13 (48) | 47 (64) | 0.163 |
| Age - median [IQR] | 78 [72-72] | 77 [71.25-83] | 80 [75-84.5] | 0.142 |
| Examination variables | | | | |
| BP systolic (mmHg) - median [IQR] | 115 [100-100] | 120 [106.25-138.75] | 105 [80-120] | 0.001 |
| BP diastolic (mmHg) - median [IQR] | 65 [60-60] | 65 [60-85] | 60 [50-70] | 0.002 |
| HR - median [IQR] | 100 [94-94] | 100 [94-114.75] | 100 [93.5-107.5] | 0.407 |
| RR - median [IQR] | 24 [22-22] | 24 [22-28] | 26 [24-28] | 0.069 |
| MAP (mmHg) - median [IQR] | 83.3 [74-74] | 83.3 [77.62-100.75] | 81.6 [63.5-89] | 0.026 |

TABLE 5-continued

| Variable | all (n = 101) | in hospitaldeaths (n = 27) | discharged (n = 74) | p-value |
|---|---|---|---|---|
| concomitantdiseases | | | | |
| Cardiovascular-yes | 26 (25.7) | 9 (33.3) | 17 (23) | 0.311 |
| Hypertensive-yes | 47 (46.5) | 13 (48.1) | 34 (45.9) | 1.000 |
| Diabetes -yes | 35 (34.7) | 9 (33.3) | 26 (35.1) | 1.000 |
| Cancere-yes | 13 (12.9) | 3 (11.1) | 10 (13.5) | 1.000 |
| routinelabaratory variables | | | | |
| Blood culture-yes | 31 (31) | 5 (19) | 26 (35) | 0.246 |
| negative | 15 (16.3) | 2 (8) | 13 (19.4) | |
| positive | 16 (17.4) | 3 (12) | 13 (19.4) | |
| Creatinine clearance (ml/min) - median [IQR] | 48 [23.25-23.25] | 56 [29.25-80] | 31.5 [14.75-66] | 0.043 |
| Creatinine - median [IQR] | 1.3 [0.9-0.9] | 1.25 [0.9-2.08] | 1.8 [1-3.15] | 0.080 |
| UREA - median [IQR] | 36 [21-21] | 31.5 [20-53.25] | 51 [42-87] | 0.004 |
| GCS - median [IQR] | 15 [10-10] | 15 [12.5-15] | 8 [8-11] | <0.001 |
| Pcr - median [IQR] | 16 [6.6-6.6] | 14.5 [6.7-23.7] | 17.35 [6.6-28.05] | 0.846 |
| Gluco - median [IQR] | 113.5 [94.5-94.5] | 110 [95.5-144] | 128 [94-160.5] | 0.400 |
| biliru - median [IQR] | 0.9 [0.71-0.71] | 0.9 [0.7-1.03] | 0.91 [0.77-1.18] | 0.534 |
| GR - median [IQR] | 3.8 [3.3-3.3] | 3.8 [3.2-4.3] | 3.7 [3.4-4.2] | 0.684 |
| GB - median [IQR] | 12700 [6774-6774] | 13100 [8115-17565] | 11920 [25.55-18790] | 0.343 |
| PLT - median [IQR] | 213 [150-150] | 217 [154.75-301] | 185 [130-236.5] | 0.113 |
| HCT - median [IQR] | 32 [28-28] | 31.5 [28-37] | 34 [31.25-39.5] | 0.149 |
| Leuco/Neutr (%) - median [IQR] | 87 [80-80] | 86 [78.25-89.95] | 91 [87-93.05] | 0.001 |
| HB - median [IQR] | 10.4 [9.47-9.47] | 10.15 [9.3-12.4] | 10.85 [9.9-12.67] | 0.220 |
| Na - median [IQR] | 137 [134-134] | 137 [133-141] | 139 [134-144.5] | 0.204 |
| K - median [IQR] | 3.9 [3.5-3.5] | 3.9 [3.6-4.3] | 3.9 [3.3-5.1] | 0.982 |
| INR - median [IQR] | 1.19 [1.1-1.1] | 1.19 [1.1-1.4] | 1.18 [1.04-1.36] | 0.731 |
| TC - median [IQR] | 38.4 [36-36] | 38.5 [38.12-38.7] | 36 [35.55-38.5] | <0.001 |
| SAO2 - median [IQR] | 94 [90-90] | 95 [90.25-97] | 93 [88.5-95.5] | 0.119 |
| pH - median [IQR] | 7.45 [7.38-7.38] | 7.46 [7.4-7.5] | 7.4 [7.24-7.4] | <0.001 |
| PO2 - median [IQR] | 67 [56-56] | 66.5 [56-78] | 67 [56.5-79.5] | 0.806 |
| PCO2 - median [IQR] | 36 [32-32] | 37.5 [33-43.75] | 34 [30-41] | 0.245 |
| Lact - median [IQR] | 1.5 [1-1] | 1.3 [0.83-1.9] | 2.5 [1.4-4.15] | <0.001 |
| Bic - median [IQR] | 23.5 [21-21] | 24.25 [21.43-28] | 21 [17.35-23.25] | 0.001 |
| FiO2 (%) - median [IQR] | 21 [21-21] | 21 [21-23.25] | 24 [21-45] | <0.001 |
| other | | | | |
| Acuteorgandisfunction-yes | 39 (43.3) | 16 (64) | 23 (35.4) | 0.021 |
| Apache score (%) - median [IQR] | 19 [12.5-12.5] | 14.65 [12.12-20.38] | 32 [20-39] | <0.001 |
| Days hospitalized - median [IQR] | 5 [2-2] | 6 [4-7] | 2 [1-6] | 0.003 |
| treatmentatbaseline | | | | |
| Diuresis (cc) - median [IQR] | 900 [600-600] | 1000 [700-1200] | 450 [200-1025] | <0.001 |
| Steroids -yes | 16 (15.8) | 4 (14.8) | 12 (16.2) | 1.000 |
| Vasopressors-yes | 18 (17.8) | 13 (48.1) | 5 (6.8) | <0.001 |
| Antibiotics-yes | 101 (100) | 27 (100) | 74 (100) | 1.000 |
| Fluid therapy-yes | 101 (100) | 27 (100) | 74 (100) | 1.000 |
| newbiomarker | | | | |
| ADM (pg/mL) - median [IQR] | 53.8 [37.4-94.0] | 93.9 [48.7-241] | 50.1 [32.2-77.8] | <0.001 |
| MR-proADM (nmol/L) [IQR] | 0.54 [0.32-0.86] | 0.98 [0.42-18.4] | 0.46 [0.28-0.82] | <0.001 |

26.7% of all patients died during hospital stay and are counted as treatment non responder, 73.3% of all patients survived the sepsis and are counted as treatment responder.

66% off all patients presenting with sepsis had a non-normal ADM value>43 pg/ml (99th percentile), indicating ADM not to be a marker for the infection.

Results of Clinical Study

Initial ADM is Highly Prognostic.

We correlated the initial ADM value with the in hospital mortality and compared ADM with APACHE 2 score. ADM is highly prognostic for sepsis outcome (see FIG. 2) and comparable to APACHE 2 score. There is a significant added information if ADM and APACHE 2 are combined (FIG. 3).

ADM in Treatment Monitoring.

Patients were treated based on standard of care treatments (table 5). The average hospitalization time was 5 days. ADM was measured each day in hospital (day 1=admission) and correlated to in hospital mortality (table 6). ADM changed during hospital stay and the change during time improved the prognostic value by 52% from initial $Chi^2$ of 19.2 to 29.2 on day 5.

Using a simple cut off model at 70 pg/ml of ADM showed a 68% risk of death for patients starting at ADM concentrations>70 pg/ml and remain all the hospital stay>70 pg/ml (treatment non-responder). Patients having all time an ADM value<70 pg/ml or developing from >70 pg/ml to <70 pg/ml had a mortality of only 11% (well treated/treatment responder) and patients presenting with ADM values>70 pg/ml and reducing their ADM concentration during hospital treatment to values<70 pg/ml had a 0% mortality. There were no patients developing from <70 pg/ml to >70 pg/ml during hospital treatment. The average time needed to generate responder/nonresponder information for all patients was about 1 day. The >70 pg/ml—patients responding to treatment during hospital stay needed about 2 days to indicate treatment success by ADM.

TABLE 6

|  | Patient all days >70 pg/ml | Patient all days <70 pg/ml | Patients changed from >70 pg/ml to <70 pg/ml |
|---|---|---|---|
| N | 28/101 (27.7%) | 73/101 (72.3%) | 15/73 (20.5%) |
| Mortality | 68% | 11% | 0% |
| Average days after hospitalization of change from ADM >70 pg/ml to ADM <70 pg/ml or no change | 1 day | 1.2 days | 2.2 days |

Relation of Plasma ADM with Mean Arterial Pressure (MAP) and Need for Vasopressor Therapy We found a significant correlation of ADM concentrations with mean arterial pressure (FIG. 4) and with the requirement for vasopressor therapy to treat/prevent shock (FIG. 5).

We also investigated the temporal relationship of ADM concentrations and the requirement for vasopressor therapy (FIG. 6): Of the 101 patients investigated, already 18 required vasopressor therapy at admission; the median ADM concentration for these patients at admission was 129 pg/mL. Patients, who never required vasopressor therapy during their hospital stay within the first four days after admission (n=79), had a median ADM concentration of 48.5 pg/mL. Importantly, patients, who required vasopressor therapy during their hospital stay later than on admission had elevated ADM levels already at admission (median 87.2 pg/mL), e.g.: the elevation of plasma ADM concentration was preceding the vasopressor therapy.

In the plasma samples also MR-proADM, a stable fragment of the ADM precursor molecule, was measured. MR-proADM has been proposed as a surrogate marker for mature ADM release (Struck J, Tao C, Morgenthaler N G, Bergmann A: Identification of an Adrenomedullin precursor fragment in plasma of sepsis patients. Peptides 2004, 25(8):1369-1372, Morgenthaler N G, Struck J, Alonso C, Bergmann A: Measurement of midregional proadrenomedullin in plasma with an immunoluminometric assay. Clinical chemistry 2005, 51(10):1823-1829). A commercial MR-proADM Assay was used (BRAHMS MR-proADM KRYPTOR) according to the instructions of the manufacturer (BRAHMS GmbH, Hennigsdorf, Germany). Median levels for the day of admission were 0.63 nmol/L for patients not requiring vasopressor therapy, and 1.57 nmol/L for patients requiring vasopressor therapy. Concentrations of MR-proADM were significantly correlated with concentrations of ADM (r=0.79).

EXAMPLE 7

Cut Off Analysis for Diagnosis and Prediction of Vasopressor Need.

Patient data see Example 6. The analysis was performed based on the first blood draw taken during emergency unit presentation of the sepsis patient.

A cut off value of 70 pg/ml was selected, <70 pg/ml indicated a low risk of vasopressor need and >70 pg/ml indicated a high risk of vasopressor need. Group 1 are patients not needed Vasopressors (MAP<=66 mmHg) nor received Vasopressors at presentation nor during a 4 day follow up period. Group 2 are Patients with Vasopressor need (MAP<=66 mmHg) or received Vasopressors at presentation. Group 3 are patients without Vasopressor need nor received Vasopressors at presentation but developed Vasopressor need during a 4 day follow up period. Patients (n=2) with missing information about Vasopressor treatment were excluded.

TABLE 7

|  | <70 pg/ml ADM | >70 pg/ml ADM |  |
|---|---|---|---|
| Group 1 | 56 | 15 | 79% specificity |
| Group 2 | 3 | 18 | 89.5% sensitivity |
| Group 3 | 2 | 5 | 71% correct classification |

Using a simple cut off analysis at 70 pg/ml 89.5% of all patients needing vasopressors at ED presentation were identified by ADM (group 2). There were 20 patients>70 pg/ml having no vasopressor need at presentation (group 1/3), 15 (75%) did not developed vasopressor need during 4 day follow up and 5 (25%) of patients developed Vasopressor need during a 4 day follow up. In contrast, if ADM was <70 pg/ml at patients without vasopressor need at presentation (Group 1/3), 56 (96.5%) did not developed vasopressor need during the 4 day follow up and only 2 (3.5%) developed a vasopressor need. The risk of developing vasopressor need during next 4 days of patients with an ADM value above 70 pg/ml is 7.1 times higher than for patients with ADM levels below 70 pg/ml (25% vs 3.5%).

Since blood pressure is always monitored, from a clinical point of view, patients with high ADM (>70 pg/ml) without vasopressor need at presentation should be vasopressor treated by adapting the points of decision from <66 mmHg MAP to e.g. <75 mmHg aiming earlier support of circulation to protect patient from low blood pressure associated organ dysfunctions and subsequent high mortality. Using this rule for patients>70 pg/ml ADM and treating with vasopressors at MAP<=75 mmHg, patients (Group 3) would be treated in average 1.6 days before standard of care treatment (<=66 mmHg).

Similar results were obtained, when MR-proADM with a cut-off value of 0.78 noml/L was used in the analysis instead of ADM.

TABLE 8

|  | <0.78 noml/L MR-proADM | >0.78 noml/L MR-proADM |  |
|---|---|---|---|
| Group 1 | 54 | 17 | 76.1% specificity |
| Group 2 | 4 | 17 | 81% sensitivity |
| Group 3 | 2 | 5 | 71% correct classification |

EXAMPLE 8

Clinical Study/Acute Heart Failure

Recruited patients were patients admitted to the emergency department with acute heart failure. Patient characteristics: Mean±SD age 74.3±12.2 y; n=1022 (643 male, 63%); previous Ischemic Heart Disease 31%, hypertension 58%, Diabetes 33%, Heart failure 35%. Patients were followed up for 2 years. Plasma samples for measurement of ADM and other analytes were gained on the day of admission.

Cox analysis revealed that ADM was an independent predictor of 1 year death (table 9) and 1 year death/hospitalization due to acute decompensated Heart Failure (table 10). Logistic regression analysis revealed that ADM was an independent predictor of in hospital death (table 11).

Patients who required vasopressor therapy (inotropes) had significantly higher ADM concentrations that all other patients (area under the curve=0.75; p<0001; FIG. 7).

TABLE 9

|  | Hazard Ratio (P value) Univariate | Hazard Ratio (P value) Multivariate |
|---|---|---|
| Age | 1.04 (<0.0005) | 1.04 (<0.0005) |
| Past history HF | 1.48 (<0.001) | N.S. |
| Past history Renal failure | 1.79 (<0.0005) | N.S. |
| Heart rate | 0.99 (<0.003) | N.S. |
| Systolic BP | 0.98 (<0.0005) | 0.98 (<0.0005) |
| Respiratory rate | 1.02 (<0.0005) | 1.02 (<0.001) |
| NYHA | 1.61 (<0.0005) | N.S. |
| Urea | 1.03 (<0.0005) | 1.05 (<0.0005) |
| Creatinine | 1.003 (<0.0005) | N.S. |
| Na | 0.96 (<0.0005) | 0.95 (<0.0005) |
| NTproBNP | 2.73 (<0.0005) | N.S. |
| ADM | 3.92 (<0.0005) | 2.35 (<0.0005) |

TABLE 10

|  | Hazard Ratio (P value) Univariate | Hazard Ratio (P value) Multivariate |
|---|---|---|
| Age | 1.02 (<0.0005) | 1.02 (<0.001) |
| Past history HF | 1.72 (<0.001) | 1.33 (<0.023) |
| Past history Renal failure | 1.75 (<0.0005) | N.S. |
| Heart rate | 0.99 (<0.002) | N.S. |
| Systolic BP | 0.99 (<0.0005) | 0.99 (<0.012) |
| Respiratory rate | 1.01 (<0.008) | 1.02 (<0.0005) |
| NYHA | 1.53 (<0.0005) | 1.29 (<0.018) |
| Urea | 1.03 (<0.0005) | 1.05 (<0.0005) |
| Creatinine | 1.002 (<0.0005) | N.S. |
| Na | 0.98 (<0.012) | 0.98 (<0.03) |
| NTproBNP | 1.82 (<0.0005) | N.S. |
| ADM | 2.75 (<0.0005) | 1.67 (<0.01) |

TABLE 11

|  | Odds Ratio (P value) Univariate | Odds Ratio (P value) Multivariate |
|---|---|---|
| Age | 1.04 (<0.001) | 1.04 (<0.039) |
| Past history HF | 1.98 (<0.007) | 1.33 (<0.023) |
| Past history Renal failure | 2.71 (<0.0005) | N.S. |
| Heart rate | 0.99 (<0.074) | N.S. |
| Systolic BP | 0.99 (<0.071) | N.S. |
| Respiratory rate |  | N.S. |
| NYHA | 1.67 (<0.023) | N.S. |
| Urea | 1.078 (<0.0005) | 1.069 (<0.015) |
| Creatinine | 1.008 (<0.0005) | N.S. |
| Na | 0.929 (<0.0005) | 0.916 ((<0.0005) |
| Troponin I | N.S. | N.S. |
| NTproBNP | 3.22 (<0.001) | N.S. |
| ADM | 10.75 (<0.0005) | 5.182 (<0.001) |

LITERATURE (1) Kitamura, K., et al., "Adrenomedullin: A Novel Hypotensive Peptide Isolated From Human Pheochromocytoma", Biochemical and Biophysical Research Communications, Vol. 192 (2), pp. 553-560 (1993).

(2) Editorial, Takahashi, K., "Adrenomedullin: from a pheochromocytoma to the eyes", Peptides, Vol. 22, p. 1691 (2001).

(3) Eto, T., "A review of the biological properties and clinical implications of adrenomedullin and proadrenomedullin N-terminal 20 peptide (PAMP), hypotensive and vasodilating peptides", Peptides, Vol. 22, pp. 1693-1711 (2001).

(4) Hinson, et al., "Adrenomedullin, a Multifunctional Regulatory Peptide", Endocrine Reviews, Vol. 21(2), pp. 138-167 (2000).

(5) Kitamura, K., et al., "The intermediate form of glycine-extended adrenomedullin is the major circulating molecular form in human plasma", Biochem. Biophys. Res. Commun., Vol. 244(2), pp. 551-555 (1998). Abstract Only.

(6) Pio, R., et al., "Complement Factor H is a Serum-binding Protein for Adrenomedulli, and the Resulting Complex Modulates the Bioactivities of Both Partners", The Journal of Biological Chemistry, Vol. 276(15), pp. 12292-12300 (2001).

(7) Kuwasako, K., et al., "Purification and characterization of PAMP-12 (PAMP-20) in porcine adrenal medulla as a major endogenous biologically active peptide", FEBS Lett, Vol. 414(1), pp. 105-110 (1997). Abstract Only.

(8) Kuwasaki, K., et al., "Increased plasma proadrenomedullin N-terminal 20 peptide in patients with essential hypertension", Ann. Clin. Biochem., Vol. 36 (Pt. 5), pp. 622-628 (1999). Abstract Only.

(9) Tsuruda, T., et al., "Secretion of proadrenomedullin N-terminal 20 peptide from cultured neonatal rat cardiac cells", Life Sci., Vol. 69(2), pp. 239-245 (2001). Abstract Only.

(10) EP 0 622 458 A2, Shionogi & Co. Ltd.; Kangawa, Kenji

(11) Hirata, et al., "Increased Circulating Adrenomedullin, a Novel Vasodilatory Peptide, in Sepsis", Journal of Clinical Endocrinology and Metabolism, Vol. 81(4), pp. 1449-1453 (1996).

(12) Ehlenz, K., et al., "High levels of circulating adrenomedullin in severe illness: Correlation with C-reactive protein and evidence against the adrenal medulla as site of origin", Exp Clin Endocrinol Diabetes, Vol. 105, pp. 156-162 (1997).

(13) Tomoda, Y., et al., "Regulation of adrenomedullin secretion from cultured cells", Peptides, Vol. 22, pp. 1783-1794 (2001).

(14) Ueda, S., et al., "Increased Plasma Levels of Adrenomedullin in Patients with Systemic Inflammatory Response Syndrome", Am. J. Respir. Crit. Care Med., Vol. 160, pp. 132-136 (1999).

(15) Wang, P., "Andrenomedullin and cardiovascular responses in sepsis", Peptides, Vol. 22, pp. 1835-1840 (2001).

(16) Wang P: Adrenomedullin in sepsis and septic shock. Shock 1998, 10(5):383-384.

(17) Wang P, Ba Z F, Cioffi W G, Bland K I, Chaudry I H: The pivotal role of adrenomedullin in producing hyperdynamic circulation during the early stage of sepsis. Archives of surgery 1998, 133(12):1298-1304.

(18) Parlapiano, C., et al.; "Adrenomedulin assay and its clinical significance", European Review for Medical and Pharmacological Sciences, 1999; 3:53-61
(19) Nishio K, Akai Y, Murao Y, Doi N, Ueda S, Tabuse H, Miyamoto S, Dohi K, Minamino N, Shoji H et al: Increased plasma concentrations of adrenomedullin correlate with relaxation of vascular tone in patients with septic shock. *Critical care medicine* 1997, 25(6):953-957.
(20) Krzeminski K, Mikulski T, Kruk B, Nazar K: Plasma adrenomedullin response to maximal exercise in healthy subjects. *Journal of physiology and pharmacology: an official journal of the Polish Physiological Society* 2003, 54(2):225-232.
(21) Dellinger R P, Levy M M, Rhodes A, Annane D, Gerlach H, Opal S M, Sevransky J E, Sprung C L, Douglas I S, Jaeschke R et al: Surviving sepsis campaign: international guidelines for management of severe sepsis and septic shock: 2012. *Critical care medicine* 2013, 41(2):580-637.
(22) Angus D C, Linde-Zwirble W T, Lidicker J, Clermont G, Carcillo J, Pinsky M R: Epidemiology of severe sepsis in the United States: analysis of incidence, outcome, and associated costs of care. *Critical care medicine* 2001, 29(7):1303-1310.
(23) Martin G S, Mannino D M, Eaton S, Moss M: The epidemiology of sepsis in the United States from 1979 through 2000. *The New England journal of medicine* 2003, 348(16):1546-1554.
(24) Melamed A, Sorvillo F J: The burden of sepsis-associated mortality in the United States from 1999 to 2005: an analysis of multiple-cause-of-death data. *Critical care* 2009, 13(1):R28.
(25) Overgaard C B, Dzavik V: Inotropes and vasopressors: review of physiology and clinical use in cardiovascular disease. *Circulation* 2008, 118(10):1047-1056.
(26) Bangash M N, Kong M L, Pearse R M: Use of inotropes and vasopressor agents in critically ill patients. *British journal of pharmacology* 2012, 165(7):2015-2033.
(27) Boucheix O B, Milano S P, Henriksson M, Reinheimer T M: Selepressin, a New V1A Receptor Agonist: Hemodynamic Comparison to Vasopressin in Dogs. *Shock* 2013.
(28) Bracht H, Calzia E, Georgieff M, Singer J, Radermacher P, Russell J A: Inotropes and vasopressors: more than haemodynamics! *British journal of pharmacology* 2012, 165(7):2009-2011.
(29) Singer M, Coluzzi F, O'Brien A, Clapp L H: Reversal of life-threatening, drug-related potassium-channel syndrome by glibenclamide. *Lancet* 2005, 365 (9474): 1873-1875.
(30) Warrillow S, Egi M, Bellomo R: Randomized, double-blind, placebo-controlled crossover pilot study of a potassium channel blocker in patients with septic shock. *Critical care medicine* 2006, 34(4):980-985.
(31) Bakker J, Grover R, McLuckie A, Holzapfel L, Andersson J, Lodato R, Watson D, Grossman S, Donaldson J, Takala J et al: Administration of the nitric oxide synthase inhibitor NG-methyl-L-arginine hydrochloride (546C88) by intravenous infusion for up to 72 hours can promote the resolution of shock in patients with severe sepsis: results of a randomized, double-blind, placebo-controlled multicenter study (study no. 144-002). *Critical care medicine* 2004, 32(1):1-12.
(32) Lopez A, Lorente J A, Steingrub J, Bakker J, McLuckie A, Willatts S, Brockway M, Anzueto A, Holzapfel L, Breen D et al: Multiple-center, randomized, placebo-controlled, double-blind study of the nitric oxide synthase inhibitor 546C88: effect on survival in patients with septic shock. *Critical care medicine* 2004, 32(1):21-30.
(33) Kirov M Y, Evgenov O V, Evgenov N V, Egorina E M, Sovershaev M A, Sveinbjornsson B, Nedashkovsky E V, Bjertnaes L J: Infusion of methylene blue in human septic shock: a pilot, randomized, controlled study. *Critical care medicine* 2001, 29(10): 1860-1867.
(34) Juffermans N P, Vervloet M G, Daemen-Gubbels C R, Binnekade J M, de Jong M, Groeneveld A B: A dose-finding study of methylene blue to inhibit nitric oxide actions in the hemodynamics of human septic shock. *Nitric oxide: biology and chemistry/official journal of the Nitric Oxide Society* 2010, 22(4):275-280.
(35) Morgenthaler N G, Struck J, Alonso C, Bergmann A: Measurement of midregional proadrenomedullin in plasma with an immunoluminometric assay. *Clinical chemistry* 2005, 51(10):1823-1829.
(36) Struck J, Tao C, Morgenthaler N G, Bergmann A: Identification of an Adrenomedullin precursor fragment in plasma of sepsis patients. *Peptides* 2004, 25(8):1369-1372.

The invention claimed is:

1. A method comprising:
providing a sample having a complex comprising at least one binder to SEQ ID No. 1 and/or fragments thereof in a bodily fluid obtained from a subject who is not suffering from a physiological shock state wherein said bodily fluid is selected from the group consisting of human citrate plasma, heparin plasma, EDTA plasma, whole blood, and serum, and
wherein said subject has a mean arterial pressure of 70 mm Hg or above and a level of proADM (SEQ ID No. 1) and/or said fragments thereof in the bodily fluid of said subject is above 90 pg/ml.

2. The method of claim 1, wherein the at least one binder comprises at least a first and second binder, wherein the first binder is selected from the group consisting of binders that bind to a region comprised within the sequence of ADM (SEQ ID No. 4) and ADM 1-52-Gly (SEQ ID No. 5); and the second binder is selected from the group consisting of binders that bind to a region comprised within the sequence of ADM (SEQ ID No. 4) and mature ADM 1-52-Gly (SEQ ID No. 5).

3. The method of claim 2, wherein said first and second binders exhibit a binding affinity to proADM (SEQ ID No. 1) and/or said fragments thereof of at least $10^7 M^{-1}$.

4. The method of claim 2, wherein said first and second binder are is-labeled in order to be detected.

5. The method of claim 2, wherein said first and second binders are bound to a solid phase.

6. The method of claim 1, wherein the at least one binder comprises at least one binder that binds to a region comprised within the sequence of MR-proADM (SEQ ID No. 3) and at least one binder that binds to a region comprised within the sequence of MR-proADM (SEQ ID No. 3).

7. The method of claim 1, wherein the at least one binder comprises at least one binder that binds to a region comprised within the sequence of CT-proADM (SEQ ID No. 6) and at least one binder that binds to a region comprised within the sequence of CT-proADM (SEQ ID No. 6).

8. The method of claim 1, wherein said at least one binder is selected from the group consisting of a proADM specific antibody, a proADM specific antibody fragment, a proADM specific non-Ig (non-immunoglobulin) scaffold binding to proADM (SEQ ID No. 1) and said fragments thereof.

9. A method comprising:
providing a vasopressor to a subject in need thereof, wherein said subject is not suffering from a physiological shock state and is identified as having a level of proADM (SEQ ID No. 1) and/or fragments thereof in a sample of bodily fluid of said subject which is above a threshold, wherein said sample is selected from the group consisting of human citrate plasma, heparin plasma, EDTA plasma, whole blood, and serum,
wherein said proADM (SEQ ID No. 1) and/or said fragments thereof are selected from the group consisting of Adrenomedullin, ADM, (SEQ ID No. 4), ADM 1-52-Gly (SEQ ID No. 5), Midregional-pro-Adrenomedullin MR-proADM, (SEQ ID No. 3), C-terminal Proadrenomedullin CT-proADM, (SEQ ID No. 6), Proadrenomedullin N-20 terminal peptide (SEQ ID No. 2), and proADM (SEQ ID No. 1) and wherein a vasopressor is selected from the group consisting of adrenaline, catecholamines, phosphodiesterase inhibitors, vasopressin, levosimendan, vasopressin V 1a receptor agonists, anti-Adrenomedullin antibodies, inhibitors of ATP-dependent K channels, inhibitors of NOS and of c-GMP,
wherein a threshold for plasma ADM and/or fragments thereof of 90 pg/ml or 70 pg/ml is applied and wherein a threshold for plasma MR-proADM and/or fragments thereof of 0.9 nmol/L or 0.7 nmol/L is applied.

10. The method of claim 9, wherein said subject has >66 mmHg Mean Arterial Pressure (MAP).

11. The method of claim 10, wherein the subject has a mean arterial pressure of 75 mmHg or above.

12. The method of claim 10, wherein the subject has a mean arterial pressure of 80 mm Hg or above.

* * * * *